US012287330B2

(12) United States Patent
Rachamim et al.

(10) Patent No.: US 12,287,330 B2
(45) Date of Patent: Apr. 29, 2025

(54) ANALYTE DETECTION AND METHODS THEREFOR

(71) Applicant: SENZO HEALTH LIMITED, Altrincham (GB)

(72) Inventors: Aron Rachamim, London (GB); Jacob Raby, London (GB)

(73) Assignee: SENZO HEALTH LIMITED, Altrincham (GB)

( * ) Notice: Subject to any disclaimer, the term of this patent is extended or adjusted under 35 U.S.C. 154(b) by 192 days.

(21) Appl. No.: 17/366,233

(22) Filed: Jul. 2, 2021

(65) Prior Publication Data

US 2021/0405033 A1 Dec. 30, 2021

Related U.S. Application Data

(62) Division of application No. 15/566,480, filed as application No. PCT/EP2016/059438 on Apr. 27, 2016, now Pat. No. 11,061,024.

(Continued)

(51) Int. Cl.
*G01N 33/537* (2006.01)
*G01N 15/06* (2006.01)
(Continued)

(52) U.S. Cl.
CPC ....... *G01N 33/537* (2013.01); *G01N 15/0618* (2013.01); *G01N 15/1456* (2013.01); *G01N 33/491* (2013.01); *G01N 33/5094* (2013.01); *G01N 33/56933* (2013.01); *G01N 33/56966* (2013.01); *G01N 33/56972* (2013.01); *G01N 2015/016* (2024.01); *G01N 15/0625* (2013.01);
(Continued)

(58) Field of Classification Search
CPC .. G01N 33/53; G01N 33/5306; G01N 33/537; G01N 33/543; G01N 33/582
See application file for complete search history.

(56) References Cited

U.S. PATENT DOCUMENTS

| 5,426,028 A | 6/1995 | Levy et al. |
| 7,256,008 B2 * | 8/2007 | Spring ............... G01N 33/9493 435/7.1 |

(Continued)

FOREIGN PATENT DOCUMENTS

| CN | 100399027 A | 4/2005 |
| CN | 101013137 A | 8/2007 |

(Continued)

OTHER PUBLICATIONS

Intellectual Property India, First Examination Report for Corresponding Indian Patent Application No. 201727042682, dated Jul. 5, 2023, 9pp.

(Continued)

*Primary Examiner* — Gailene Gabel
(74) *Attorney, Agent, or Firm* — The Roy Gross Law Firm, LLC; Roy Gross

(57) ABSTRACT

Disclosed are methods and systems for analyte detection in a sample and more particularly, a biological sample. Methods and systems particularly relate to differentiating and/or identifying cell types in biological samples, such as blood samples, by adding antibodies specific to predetermined CD antigens. Other methods and systems relate to controlling the dynamic range of an assay for analyte detection.

7 Claims, 18 Drawing Sheets

Related U.S. Application Data

(60) Provisional application No. 62/155,486, filed on May 1, 2015, provisional application No. 62/153,523, filed on Apr. 28, 2015.

(51) Int. Cl.
  *G01N 15/14* (2006.01)
  *G01N 33/49* (2006.01)
  *G01N 33/50* (2006.01)
  *G01N 33/569* (2006.01)
  *G01N 15/01* (2024.01)
  *G01N 35/00* (2006.01)

(52) U.S. Cl.
  CPC .......... *G01N 2015/1486* (2013.01); *G01N 2015/1488* (2013.01); *G01N 2035/00475* (2013.01)

(56) References Cited

U.S. PATENT DOCUMENTS

| | | |
|---|---|---|
| 8,377,398 B2 | 2/2013 | McDevitt et al. |
| 2003/0175828 A1 | 9/2003 | Lazar |
| 2007/0161123 A1 | 7/2007 | Spring et al. |
| 2007/0190653 A1 | 8/2007 | Heinrich |
| 2007/0218062 A1 | 9/2007 | Irving |
| 2010/0015638 A1 | 1/2010 | Uchiyama et al. |
| 2010/0189338 A1 | 7/2010 | Lin et al. |
| 2014/0227725 A1 | 8/2014 | Fagerhol |
| 2014/0273018 A1 | 9/2014 | Bystryak et al. |

FOREIGN PATENT DOCUMENTS

| | | |
|---|---|---|
| CN | 101057141 | 10/2007 |
| CN | 101443660 A | 5/2009 |
| CN | 101762688 A | 6/2010 |
| CN | 101939645 A | 1/2011 |
| CN | 102089418 A | 6/2011 |
| CN | 103869061 A | 6/2014 |
| CN | 104178454 A | 12/2014 |
| DE | 10246428 A1 | 4/2004 |
| DE | 102008008214 A1 | 9/2008 |
| EP | 1247715 A1 | 10/2002 |
| EP | 1342637 A1 | 9/2003 |
| EP | 1925523 A1 | 5/2008 |
| JP | 2007024498 A | 7/2005 |
| JP | 2009522581 A | 6/2009 |
| JP | 2011090008 A | 5/2011 |
| JP | 2015505828 A | 2/2015 |
| WO | 03100086 A1 | 12/2003 |
| WO | 2015002975 A1 | 1/2015 |

OTHER PUBLICATIONS

Third Office Action (with English translation) for corresponding Chinese Patent Application No. 201680037683.5, issue on May 27, 2021, 10 pp.

Second Office Action (with English translation) for corresponding Chinese Patent Application No. 201680037683.5, issue on Sep. 8, 2020, 12 pp.

Office Action (with English translation) for corresponding Chinese Patent Application No. 201680037683.5, issue on Jan. 17, 2020, 17 pp.

European Patent Office, Communication from the Examining Division for App. No. 167198498, Mailed Nov. 28, 2018, 8 pp.

World Health Organization (2007). "Laboratory Guidelines for 1-16 enumerating CD4 T Lymphocytes in the context of HIV/AIDS Laboratory Guidelines or enumerating CD4 T Lymphocytes in the context of HIV/AIDS", World Health Organization, Jan. 1, 2007, pp. 1-62. Retrieved from https://www.who.int/hiv/amds/LaboratoryGuideEnumeratingCD4TLymphocytes.pdf on Jul. 8, 2021.

Tomlinson et al. (2012), Cell separation: Terminology and practical considerations, Journal of Tissue Engineering, Jan. 1, J012, pp. 1-14. Retrieved from: https://journals.sagepub.com/doi/10.1177/2041731412472690 on Jul. 8, 2021.

Wosnitza et al., PAIA assays: A new bead-based assay system for high throughput protein quantification, BMC Proceedings, May 31, 2015, vol. 9, No. 9. Retrieved from: http://w1W1.biomedcentral.com/17S3-6561 /9/S9/P62 on Jul. 8, 2021.

PCT International Search Report for International Application No. PCT/EP2016/059438, Completed Jun. 14, 2016; Mailed Aug. 29, 2016, 5pp. (English translation of Search Report).

PCT Written Opinion for International Application No. PCT/EP2016/059438, mailed Aug. 29, 2016, 13 pp.

* cited by examiner

ANALYTE DETECTION AND METHODS THEREFOR

RELATED APPLICATION

This application is divisional of U.S. Ser. No. 15/566,480 filed Oct. 13, 2017, which is a national phase of PCT Patent Application No. PCT/EP2016/059438 filed Apr. 27, 2016, which claims the benefit of priority of U.S. Provisional Application No. 62/153,523, entitled "Method and System for Identifying Cells in Blood Samples by Adding Antibodies Specific to Clusters of Differentiation", filed on 28 Apr. 2015 and U.S. Provisional Application No. 62/155,486, entitled "Method and System for Controlling Dynamic Range of Assay Quantification for Analyte Detection", filed on 1 May 2015. The contents of the above applications are all incorporated by reference as if fully set forth herein in their entirety.

TECHNICAL FIELD

This technology relates to analyte detection. More particularly, this technology relates to methods and systems for identifying cell types in samples. This technology also relates to methods and systems for controlling dynamic range of assay quantification for analyte detection.

BACKGROUND

Analyte detection remains an important tool not only for medical applications but also broadly for agricultural and veterinary applications. Blood cell count is an important diagnostic tool, which provides valuable information regarding a patient's health. The complete blood count determines the number of various types of blood cells per unit volume of patient's blood. One type of blood cell that is counted is the white blood cell (WBC). High levels of white blood cells in circulation are indicative of a development of a bacterial infection and/or inflammation, and information regarding differentiation of white blood cells in a blood sample can provide one with a detailed information with respect to certain specific conditions, such as allergic reactions, leukaemia, human immunodeficiency virus (HIV), and the general state of the immune system. The elevated number of red blood cells can indicate development of a number of conditions, such as anaemia and bone marrow disorders. Change in platelet number in circulation can flag up the risk of bleeding or clots in a patient, and it can also indicate a development of a viral infection.

Clusters of differentiation (CD) antigens are membrane proteins expressed on the surface of blood cells that are widely used for an identification of different types of white blood cell, as well as erythrocytes and platelets. The nomenclature of the clusters of differentiation has been proposed and established at the First International Workshop and Conference on Human Leukocyte Differentiation Antigens (HLDA). Immunologists globally generated large numbers of monoclonal antibodies reacting with leukocyte cell surface molecules, and each of these antibodies was associated with different nomenclatures. In the absence of comparative studies, it was often impossible to tell whether the same molecule was recognised by more than one antibody. The approach of the workshops was to code and classify antibodies and to send them to multiple participating laboratories to perform a blind analysis allowing one to compare multiple cell types. The data obtained were collated and analysed by a statistical procedure of "cluster analysis." This analytical method identified clusters of antibodies with very similar patterns of binding to leukocytes at various stages of differentiation: as such, the "cluster of differentiation" (CD) nomenclature was created. The cluster of differentiation nomenclature allowed the scientific community to communicate results in a universal language.

The cluster of differentiation nomenclature defines different monoclonal antibodies from different sources that recognize identical antigens. A proposed surface molecule is assigned a CD number, once two specific monoclonal antibodies are shown to bind to the molecule. Two commonly used CD molecules are CD4 and CD8, which are, in general, used as markers for two different subtypes of T-lymphocytes, T-helpers and cytotoxic T cells, respectively. CD4 is specifically recognized and bound by HIV, which leads to a viral infection and destruction of CD4+ T cells. At the same time, in many cases, elevated proportions of CD8+ cells are observed in persons infected with HIV. Thus, the conventional approaches to diagnosing HIV infection have included monitoring CD4+ count, the percentage of CD4+ and CD4+/CD8+ ratio.

Development of methods of cell counting and differentiation started more than a century ago. One of the oldest methods for blood cell counting employs haemocytometers. These are manual cell counting devices consisting of a thick glass microscope slide with a rectangular indentation that creates a chamber. This chamber is engraved with a laser-etched grid of perpendicular lines. The device is carefully crafted so that the area bounded by the lines is known, and the depth of the chamber is also known. It is, therefore, possible to count the number of cells or particles in a specific volume of fluid, e.g., blood, and thereby calculate the concentration of cells in the fluid overall.

Another method of cell counting is called flow cytometry. It is a modem laser-based, biophysical technology employed not only in cell counting, but also in cell sorting, biomarker detection and protein engineering, by suspending cells in a stream of fluid and passing them through an electronic detection apparatus. It allows simultaneous multi-parametric analysis of the physical and chemical characteristics of up to thousands of particles per second.

Flow cytometry is routinely used in the diagnosis of health disorders, especially blood cancers, but has many other applications in basic research, clinical practice, and clinical trials. A common variation is to physically sort particles based on their properties so as to purify populations of interest.

There are also known numerous methods of pathogen detection and identification. One of the oldest methods is Gram staining. Gram staining, also called Gram's method, is a method of differentiating bacterial species into two large groups (Gram-positive and Gram-negative). Gram staining differentiates bacteria by the chemical and physical properties of their cell walls by detecting peptidoglycan, which is present in a thick layer in gram-positive bacteria. In a Gram stain test, Gram-positive bacteria retain the crystal violet dye, while a counter-stain (commonly safranin or fuchsine) added after the crystal violet gives all Gram-negative bacteria a red or pink colouring. The Gram stain is almost always the first step in the identification of a bacterial organism. While Gram staining is a valuable diagnostic tool in both clinical and research settings, not all bacteria can be definitively classified by this technique.

The polymerase chain reaction (PCR) is another technology in molecule biology used to amplify a specific region of a deoxyribonucleic acid (DNA) strand across several orders of magnitude, generating thousands to millions of copies of a particular DNA sequence. PCR permits early diagnosis of malignant diseases, such as leukaemia and lymphomas, which is currently the highest-developed in cancer research and is already being used routinely. Culturing of organisms has been also used in clinical diagnostic testing for bacterial enteric pathogens. In culturing, samples are often incubated in media selective for a pathogen being investigated, normally containing inhibitors to non-target species. The growth of the pathogen can thereafter be determined optically. These culture methods include the Microscopic Observation Drug Susceptibility assay (MODS). It is a culture method shown to be more sensitive, faster and cheaper test than current culture-based tests for tuberculosis. The Microscopic Observation Drug Susceptibility assay involves direct observation of *Mycobacterium tuberculosis* and simultaneously yields drug-resistance.

Immunomagnetic separation (IMS) is another method that can efficiently isolate cells out of body fluid or cultured cells. It can also be used as a method of quantifying the pathogenicity of food, blood or faeces. DNA analysis have supported the combined use of both this technique and PCR. Immunomagnetic separation methods are based on the attachment of small magnetisable particles to cells via antibodies or lectins. When the mixed population of cells is placed in a magnetic field, those cells that have beads attached will be attracted to the magnet and may thus be separated from the unlabelled cells. Several makes of bead are available, some of which are designed specifically for cell sorting, and others that are designed for purifying molecules (particularly nucleic acids) but that may be adapted for cell sorting if necessary. The different types of beads work on the same principle, but the strength of the magnetic field required to separate the cells differs depending on the size of the beads.

Antibody-coated paramagnetic beads will bind to antigens present on the surface of cells, thus capturing the cells and facilitate the concentration of these bead-attached cells. The concentration process is created by a magnet placed on the side of the test tube bringing the beads to it. Antibody-coated magnetic beads can be used to target antigens specific to the target pathogen, and to separate pathogens from a sample.

The enzyme-linked immunosorbent assay (ELISA) is yet another test that uses antibodies and colour change to identify a substance. ELISA is a popular format of "wet-lab" type analytic biochemistry assay that uses a solid-phase enzyme immunoassay (EIA) to detect the presence of a substance, usually an antigen, in a liquid sample or wet sample. The ELISA has been used as a diagnostic tool in medicine and plant pathology, as well as a quality-control check in various industries. Performing an ELISA involves at least one antibody with specificity for a particular antigen. A sample with an unknown amount of antigen is immobilized on a solid support (usually a polystyrene microtiter plate) either non-specifically (via adsorption to the surface), or specifically (via capture by another antibody specific to the same antigen, in a "sandwich" ELISA). After the antigen is immobilized, the detection antibody is added, forming a complex with the antigen. The detection antibody can be covalently linked to an enzyme, or can itself be detected by a secondary antibody that is linked to an enzyme through bioconjugation.

Thus, there are a number of methods of distinguishing cell types in blood samples known in the art, however these methods do not always provide satisfactory results and require complex, slow, and bulky equipment. Hence, there is still a need in the art to improve the methods for distinguishing cell types in blood samples.

Immunoassays are bioanalytical methods used for detecting the presence or quantity of one or more target analytes in a biological sample based on the principle of immuno-complexes formed by antigen-antibody interactions. These assays generally utilize antigen-antibody complexes to generate measurable signals, which indicate the quantity of one or more analytes present in the sample. Immunoassays have been widely used in disease diagnosis, drug discovery, and pharmaceutical analysis.

Different types of immunoassays are used for detection and quantification of analytes, each suited for a specific application. Enzyme immunoassay methods utilize enzyme labelled reagents for specifically binding to a target analyte (antigen or antibody). The bound reagent is quantified as a measure of enzyme activity that yields a coloured, fluorescent, luminescent, or otherwise modified product upon adding a suitable substrate such as a "development fluid." In competitive immunoassays, enzyme conjugated analytes compete with analytes present in the sample, for binding sites on capture antibodies coated onto a support surface. The greater the concentration of analyte in the sample results in lesser binding of conjugated analytes to the antibodies.

The dynamic range of an assay is the range of target analyte concentration over which an accurate measurement can be made. It important that the concentration of a target molecule in a sample is within the dynamic range of the assay. The dynamic range of the assay can be influenced by factors such as detection limits of a reading device, a rate of development of the development fluid or other substrate, incubation time, and so forth. For example, if the fluorescence signal from reporters bound to a high concentration analyte is too high, then the optical sensor (e.g., photodiode) may be saturated so it is not possible to get a precise reading of the actual light level, and therefore not possible to determine the analyte concentration. Similarly, if the rate of development of a development fluid is too fast then the development fluid may become completely developed before a measurement is taken so that it is not possible to determine exactly how fast the development fluid developed, and therefore not possible to determine the exact analyte concentration. In existing multiplexed assay methods, various strategies were adopted to enhance the dynamic range of assay performance including the use of serial dilution methods, flow cytometry bead-based platforms, and co-coupling of reagent and neutral reagent to a substrate under suitable conditions. Other methods have concentrated on increasing the dynamic range of the instrumentation used to check the signal. For example, chemiluminescence based multiplex assays facilitate determining the concentration of different target analytes by individually analysing the light emitted from antibodies bound to each region comprising different targets. However, the above methods do not always provide accurate and fast analyte detection especially in the circumstances when multiple analytes are present in a sample. Hence, there is still a need in the art for improving the methods for analyte detection.

It will be appreciated that reference herein to "preferred" or "preferably" is intended as exemplary only.

SUMMARY

In one broad form, the present technology generally relates to a method and system for differentiating and/or identifying cell types in biological samples, such as blood samples, by adding antibodies specific to predetermined CD antigens. In one embodiment, following an incubation of the antibodies allowing them to bind to the CD antigens, an initial antibody concentration can be calculated based on an amount of antibodies introduced and a sample volume. Alternatively, the blood sample could be assayed to determine an initial concentration of each antibody. Subsequently, the blood sample is filtered to separate out the cells and bound antibodies. The filtrate, or a fraction thereof is thereafter assayed again to determine a final concentration of each antibody that did not bind to surfaces of the cells. In this technology, the greater the number of cells expressing a particular CD antigen on the cell surface, the lower the concentration of antibody that will remain in the filtrate. The number and/or types of the cells expressing each CD antigen are then determined based on calculating a change in antibody concentration prior to filtration and after filtration.

In other embodiments, the number of antibodies bound to the cells are assayed directly whilst attached to the cells. In another embodiment, the number of antibodies bound the cells are assayed directly after being acted upon to delink, uncouple or unbind them from the cells. In these embodiments, the greater the number of cells expressing a particular CD antigen on the cell surface, the greater the concentration of antibody determined by the assay.

In various embodiments, CD antigens can be replaced with any other suitable cell surface proteins, or other molecules specific to cell surface of a particular cell type or group of cell types. In yet more embodiments, CD antigens may include or be substituted with any natural or synthetic protein suitable for measuring antibody concentrations as discussed herein. Moreover, antibodies could be replaced with any other type of chemical molecules with high affinity only for one particular protein (e.g., aptamers), or other cell surface molecules.

According to one aspect of this disclosure, a method for differentiating cells in a biological sample is provided. The method comprises the steps of: (i) contacting the biological sample with marker-specific molecules against at least one surface marker of the cells, where the marker-specific molecules are associated with a first count parameter; (ii) allowing the cells in the biological sample to bind to the marker-specific molecules to produce bound marker-specific molecules; (iii) filtering the biological sample by removing the cells and the bound marker-specific molecules from the biological sample to generate a filtrate; (iv) determining, by a sensor or an analyser, a second count parameter of the marker-specific molecules in the filtrate; and (v) calculating, by a computing device or the analyser, a number of the cells in the biological sample based on the difference between the first count parameter and the second count parameter.

In some embodiments, the first count parameter includes a first concentration of the marker-specific molecules, while the second count parameter includes a second concentration of the marker-specific molecules. In other embodiments, the first and second count parameters may relate to a count number.

In some embodiments, the marker-specific molecules include one or more antibodies of at least one type and/or specificity. In other embodiments, the marker-specific molecules include one or more aptamers of at least one type and/or specificity.

In some embodiments, each of the surface markers is associated with a distinct cluster of differentiation.

In some embodiments, the method may further include the step of identifying one or more types of the cells based on the difference between the first count parameter and the second count parameter. In yet more embodiments, the method may further include the step of passing the filtrate onto an analyser structure containing discrete regions, to which the surface markers are bound. In some embodiments, the method may further include the step of comprising incubating the filtrate in the analyser structure.

In some embodiments, the at least one surface marker of the cells includes one or more pathogen surface markers that facilitate identifying pathogens in the biological sample. In some embodiments, the at least one surface marker of the cells includes one or more mycoplasma surface markers that facilitate detecting mycoplasma growth in cell lines.

In some embodiments, the first count parameter of the marker-specific molecules 1s predetermined. In other embodiments, the method may further include the step of determining, by the sensor or the analyser, the first count parameter of the marker-specific molecules prior to generating the filtrate. In yet more embodiments, the method may further include the step of determining, by the computing device or the analyser, a disease of an individual based on the difference between the first count parameter and the second count parameter.

In certain embodiments, the method may further include the steps of maintaining, by the computing device or the analyser, a plurality of treatment recommendations; and providing, by the computing device or the analyser, one of the treatment recommendations based on determination of the disease of the individual.

According to another aspect of this disclosure, a method for differentiating cells in a biological sample is provided. The method comprises the steps of: (i) contacting the biological sample with marker-specific molecules against at least one surface marker of the cells, wherein the marker-specific molecules are associated with a count parameter; (ii) allowing the cells in the biological sample to bind to the marker-specific molecules to produce bound marker-specific molecules; (iii) treating or filtering the biological sample to remove the cells and the bound marker-specific molecules from the biological sample and generate a filtrate; (iv) determining, by a sensor or an analyser, a count parameter of the bound marker-specific molecules; and (v) calculating, by the analyser, a number of the cells of one or more types based on the count parameter of the marker-specific molecules and the count parameter of the bound marker-specific molecules.

According to yet another aspect of this disclosure, a system for differentiating cells in a biological sample is provided. The system comprises: (i) a sampling module configured to contact the biological sample with marker-specific molecules against at least one surface marker of the cells and allow the cells in the biological sample to bind to the marker-specific molecules to produce bound marker-specific molecules, where the marker-specific molecules are associated with a first count parameter; (ii) a filter configured to filter the biological sample by removing the cells and the bound marker-specific molecules from the biological sample to generate a filtrate; and (iii) an analyser configured to determine a second count parameter of the marker-specific molecules in the filtrate and calculate a number of the cells in the biological sample based on the difference between the first count parameter and the second count parameter.

According to yet another aspect of this disclosure, a system for differentiating cells in a biological sample is provided. The system comprises: (i) a sampling module configured to contact the biological sample with marker-specific molecules against at least one surface marker of the cells and allow the cells in the biological sample to bind to the marker-specific molecules to produce bound marker-specific molecules, where the marker-specific molecules are associated with a first count parameter; (ii) a filter configured to filter the biological sample by removing the cells and the bound marker-specific molecules from the biological sample; and (iii) an analyser configured to determine a second count parameter of the marker-specific molecule bound to the cells (either whilst bound or once acted upon to unbind them from the cell) and calculate a number of the cells in the biological sample based on the difference between the first count parameter and the second count parameter.

In some embodiments, the analyser includes a computing device having at least one processor and a memory, which stores processor-executable instructions that, when executed by the at least one processor, cause the at least one processor to determine the second concentration of the at least one marker-specific molecule in the filtrate, and calculate the number of the cells in the biological sample based on the difference between the first concentration and the second concentration.

In some embodiments, the system can be implemented as a portable and/or disposable system to provide a fast, field/point-of-care-based method applicable for cell counting and differentiation for various purposes including, but not limited to diagnostics, health monitoring, blood typing and monitoring of HIV progression, distinguishing between infections of viral or bacterial origin, pathogen detection and identification, diagnostics based on biological fluid and tissue samples, utilization in food industry, agricultural applications, water quality testing, and/or detecting mycoplasma contamination in cultured cell lines. An advantage of this technology is that it can be implemented more easily in a small form factor microfluidic system than traditional cell counting techniques such as flow cytometry. Therefore, it enables cell counting in portable systems which has many beneficial applications.

In general, the methods of this disclosure can be practiced for cell counting in any solution or suspension used for commercial and non-commercial applications, which may contain organic or inorganic components. For example, the methods of this disclosure can be practiced for any biological fluid derived from a human, animal, or related to any biological organism, including plants, fungi, bacteria, or archaebacteria. In some embodiments, the methods of this disclosure can be practiced for blood cell counting.

According to yet more embodiments, the methods and systems of this disclosure can be practiced for determining if a patient has a particular disease and/or if said patient requires a corresponding treatment. This determination can be based on the results of differentiating/identifying of cells in a biological sample as described herein. For example, determination of white blood cell count using the methods of this disclosure could be used to determine if an individual has an infection leading to treatment with antibiotics. In another embodiment, the determination of red blood cell count using the methods of this disclosure can be used to determine if an individual is anaemic and needs to be treated, for example, with iron supplements. In yet another embodiment, the determination of decreased white or red blood cell count may be a consequence of treatment with certain drugs, for example, clozapine. Therefore, the choice of treatment can also depend on a cell count. Determination of blood cell count and cell count in other biological samples can, therefore, be seen to be very important for treatment decisions in the medical field.

The present technology also generally relates to a method and system for quantitative detection of one or more target analytes in a biological sample by controlling the dynamic range of assay signals and, therefore, raw results. This technology allows for overcoming one or more drawbacks of the prior art and provide accurate and fast analyte detection.

According to one aspect of the technology, a method for controlling a dynamic range of assay signals is provided. The method comprises the steps of: (i) providing one or more target analytes in a sample; (ii) contacting the one or more target analytes with a mixture of a conjugated binding reagent and an unconjugated binding reagent, where the conjugated binding reagent and the unconjugated binding reagent are specific to the one or more target analytes; (iii) measuring the interaction between the one or more target analytes and the mixture of the conjugated binding reagent and the unconjugated binding reagent; and (iv) controlling a dynamic range of assay signals by adjusting a ratio of the conjugated binding reagent and the unconjugated binding reagent in the mixture.

In some embodiments, the method may further comprise the step of determining a concentration of each of the target analytes. In yet more embodiments, the method may further comprise the steps of adding one or more conjugated analytes to the sample; and causing dilution of the one or more target analytes. In yet more embodiments, the method may further comprise the steps of adding one or more unconjugated analytes to the sample; and causing dilution of the one or more target analytes.

In some embodiments, the conjugated binding reagent or the unconjugated binding reagent includes one or more of the following: an antibody, an antigen, an aptamer, a peptide, a protein, and an oligonucleotide, and any combinations thereof. The conjugated binding reagent may include a binding reagent coupled with a conjugate selected from a group consisting of: an enzyme, a protein, a peptide, a fluorophore, a streptavidin, an avidin, an antibody, an antigen, an aptamer, and an oligonucleotide, and any combinations thereof In some embodiments, the target analytes may include one or more of the following: an antigen, an antibody, a nucleic acid, a carbohydrate, a lipid, a peptide, a protein, a polymer, and any combinations thereof. In some embodiments, the sample may include a biological fluid. In other embodiments, the sample may include a non-biological fluid. In more embodiments, the method may further include the step of quantitatively determining the one or more target analytes in the sample based on results of the measuring of the interaction between the one or more target analytes and the mixture, and based on the controlling of the dynamic range of assay signals.

According to another aspect of this disclosure, there is provided another method for controlling a dynamic range of assay signals. The method comprises the steps of: (i) providing one or more target analytes in a sample; (ii) contacting the one or more target analytes with a mixture containing at least one binding reagent, wherein the binding reagent is specific to the one or more target analytes; (iii) measuring the interaction between the one or more target analytes and the mixture; (iv) adding one or more conjugated analytes to the sample to cause dilution of the one or more target analytes; and (v) controlling a dynamic range of assay signals by adjusting a ratio of the one or more conjugated analytes in the mixture.

In some embodiments, the at least one binding reagent includes an unconjugated binding reagent. In certain embodiments, the at least one binding reagent includes a conjugated binding reagent. In more embodiments, the method may further include the step of quantitatively determining the one or more target analytes in the sample based on results of the measuring of the interaction between the one or more target analytes and the mixture, and based on the controlling of the dynamic range of assay signals.

According to another aspect of this disclosure, there is provided another method for controlling a dynamic range of assay signals. The method comprises the steps of: (i) providing one or more target analytes in a sample; (ii) contacting the one or more target analytes with a mixture containing at least one binding reagent, wherein the binding reagent is specific to the one or more target analytes; (iii) measuring the interaction between the one or more target analytes and the mixture; (iv) adding one or more modified analytes to the sample; and (v) controlling a dynamic range of assay signals by adjusting a ratio of the one or more modified analytes in the mixture.

In some embodiments, the one or more modified analytes include molecules having structures that are the same as structures within the one or more target analytes. For example, the one or more modified analytes include a subunit of at least one of the target analytes. In other embodiments, the method may further include the step of adding one or more conjugated analytes to the sample to cause dilution of the one or more target analytes. In certain embodiments, the at least one binding reagent includes an unconjugated binding reagent. In some embodiments, the at least one binding reagent includes a conjugated binding reagent. In yet more embodiments, the method may further include the step of quantitatively determining the one or more target analytes in the sample based on results of the measuring of the interaction between the one or more target analytes and the mixture, and based on the controlling of the dynamic range of assay signals.

According to yet another aspect of this disclosure, there is provided a system for controlling a dynamic range of assay signals. The system comprises a container for providing one or more target analytes in a sample and contacting the one or more target analytes with a mixture of a conjugated binding reagent and an unconjugated binding reagent, wherein the conjugated binding reagent and the unconjugated binding reagent are specific to the one or more target analytes. The system further comprises a sensor configured to measure the interaction between the one or more target analytes and the mixture of the conjugated binding reagent and the unconjugated binding reagent. The system further comprises a controller configured to control a dynamic range of assay signals by adjusting a ratio of the conjugated binding reagent and the unconjugated binding reagent in the sample.

In some embodiments, the system may comprise an analyser configured to determine a concentration of each of the target analytes. In certain embodiments, the sensor may include one or more of the following: a colorimetric sensor, a fluorimetric sensor, a photometric sensor, and a spectrophotometric device. In some embodiments, the analyser may comprise a computing device operatively connected to the sensor. In some embodiments, the controller may comprise a computing device including at least one processor and a memory, which stores processor executable instructions, which when executed by the least one processor cause the system to make measurements by the sensor, change a ratio of the mixture, and quantitatively determine the one or more target analytes.

In preferred embodiments of any one of the aforementioned aspects, the ratio is selected from the group consisting a molar ratio, a weight ratio and a volumetric ratio, and any combinations thereof.

Preferably, the ratio is a molar ratio.
Preferably, the ratio is a weight ratio.
Preferably, the ratio is a volumetric ratio.

According to preferred embodiments of any one of the aforementioned aspects, the biological sample is a blood sample.

The articles "a" and "an" are used herein to refer to one or to more than one (i.e., to at least one) of the grammatical object of the article. By way of example, "an element" means one element or more than one element. As used herein, the use of the singular includes the plural (and vice versa) unless specifically stated otherwise.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Additional objects, advantages, and novel features will be set forth in part in the detailed description, which follows, and in part will become apparent to those skilled in the art upon examination of the following detailed description and the accompanying drawings or may be learned by production or operation of the example embodiments. The objects and advantages of the concepts may be realized and attained by means of the methodologies, instrumentalities, and combinations particularly pointed out in the appended claims.

BRIEF DESCRIPTION OF THE DRAWINGS

FIG. 5A shows results using anti-CD4 antibodies to determine the number of cells in a sample. In this example, a VL3 cell line with stable expression of CD surface markers was used as the test sample. Y-axis is fluorescence; the X-axis is cell count (reciprocal)=1/(cell count×10e6). MFI is mean fluorescence intensity.

In FIG. 7B, the prolactin concentration (X-axis) is plotted against against the absorbance at 450 nm (Y-axis).

Figure 1:
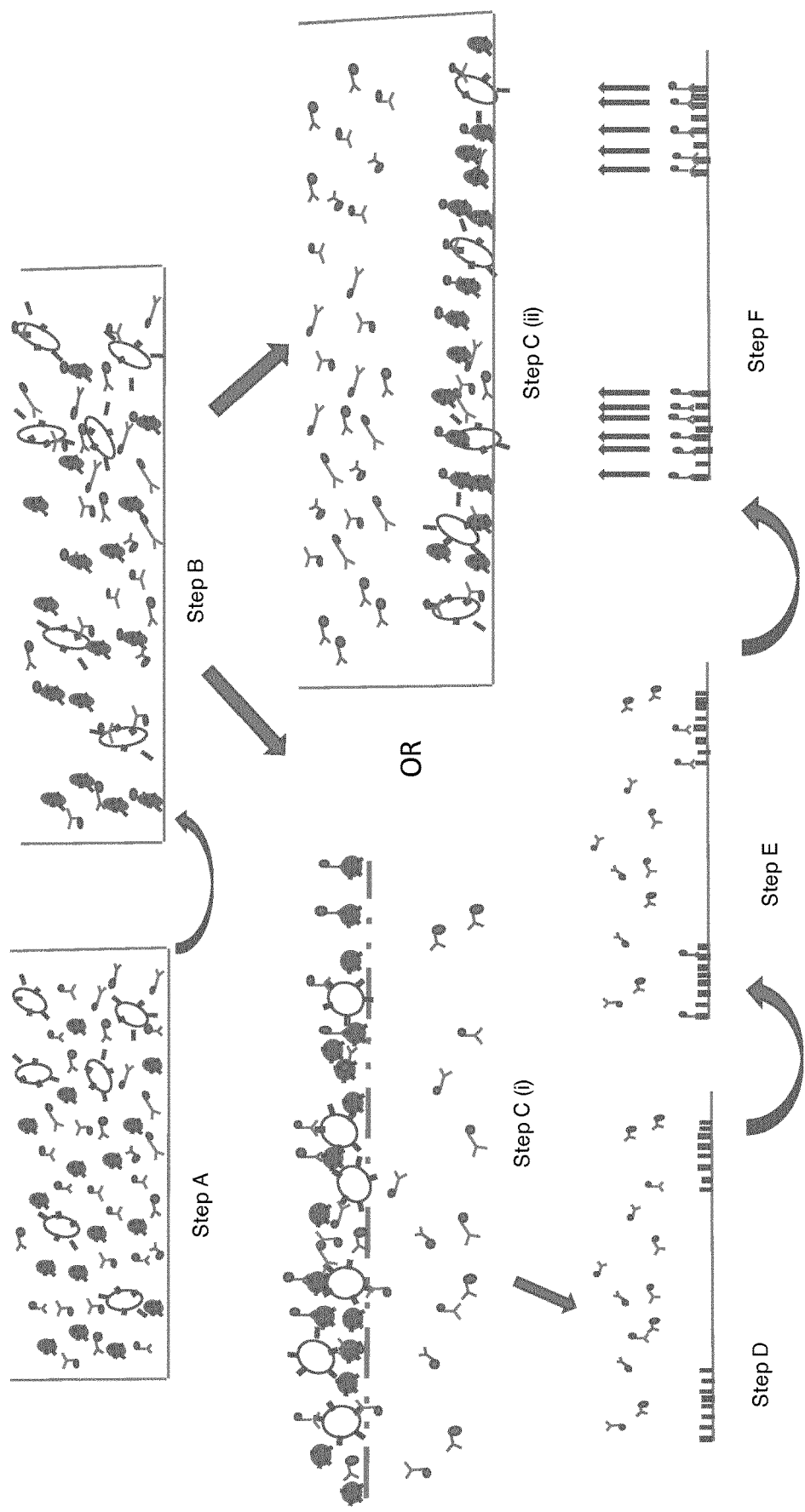
FIG. 1 is a diagrammatic representation of a method for differentiating and/or identifying cells or other components in a biological sample according to an embodiment.

Some figures contain colour representations or entities. Colour illustrations are available from the Applicant upon request or from an appropriate Patent Office. A fee may be imposed if obtained from the Patent Office.

DETAILED DESCRIPTION

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

Each embodiment described herein is to be applied mutatis mutandis to each and every embodiment unless specifically stated otherwise.

The embodiments can be combined, other embodiments can be utilized, or structural, logical and operational changes can be made without departing from the scope of what is claimed. The following detailed description is, therefore, not to be taken in a limiting sense, and the scope is defined by the appended claims and their equivalents.

In order that the invention may be readily understood and put into practical effect, particular preferred embodiments may be described by way of the non-limiting examples.

The following detailed description includes references to the accompanying drawings, which form a part of the detailed description. The drawings show illustrations in accordance with example embodiments. These example embodiments, which are also referred to herein as "examples," are described in enough detail to enable those skilled in the art to practice the present subject matter.

Method and System for Identifying Cells in Biological Samples by Adding Antibodies Specific to Clusters of Differentiation This present technology provides for a method and system for differentiating and/or identifying cells or other components (collectively referred to as "cells" for simplicity) in a biological sample such as a blood sample. Specifically, the method includes the steps of incubating the sample with multiple antibodies or other molecules such as aptamers (collectively referred to as "antibodies" for simplicity), which bind specifically to certain surface markers of the cells. The methods described herein contemplates use of one or more antibodies with one or more specificities. The number and types of specific surface markers can be preselected or predetermined such that each of the surface markers is associated with a particular CD. Further, an antibody concentration in a sample, and particularly a blood sample, is determined either through calculation or measurement. In some embodiments, the antibody concentration can be predetermined or known. The sample is subsequently filtered by separating the cells from bound antibodies to produce a filtrate. Further, the antibody concentration remaining in the filtrate is measured. Finally, the antibody concentrations before and after the filtration are compared to determine numbers and/or types of the cells in the sample. It will be appreciated that a filtrate includes a fraction thereof.

FIG. 1 further illustrates this process. Specifically, it shows the method where fluorescently labelled antibodies contact surface markers for different types of cells in a sample. A known concentration of labelled antibodies specific to surface markers on cells of interest are added to a sample (Step A). The sample is incubated with antibodies to allow binding (Step B). At Step C, the sample is either (i)

passed through a filter to remove cells and bound antibodies thus producing a filtrate containing unbound antibodies; or (ii) cells and bound antibodies are removed from the sample by sedimentation or centrifugation to produce an aspirate containing unbound antibodies. Following Step C, the filtrate is introduced to a surface with regions containing immobilised surface proteins (Step D). The filtrate is incubated to permit antibodies to bind immobilised antigens (Step E). After washing, light emittance from immobilised labelled-antibodies is measured and an antibody concentration in the filtrate is calculated (Step F). Finally, the number of each type of cell is calculated from the difference in antibody concentration pre- and post-filtration.

Figure 2A:
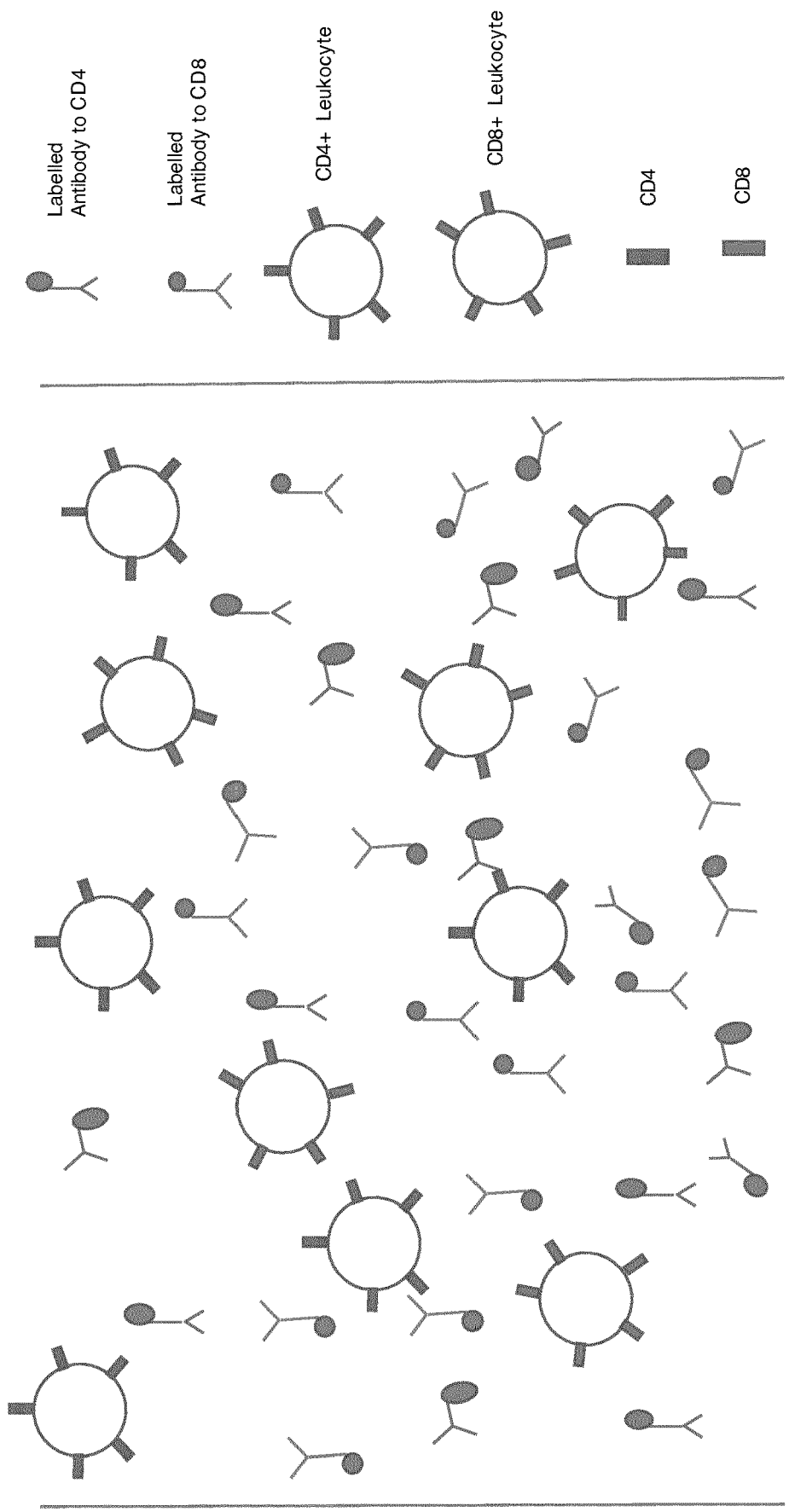
FIG. 2A is a diagrammatic representation of a further embodiment of a method for differentiating and/or identifying cells or other components in a biological sample which uses antibodies to CD4 and CD8 to determine CD4+:CD8+ ratios in a sample to assess HIV progression.
Figure 2B:
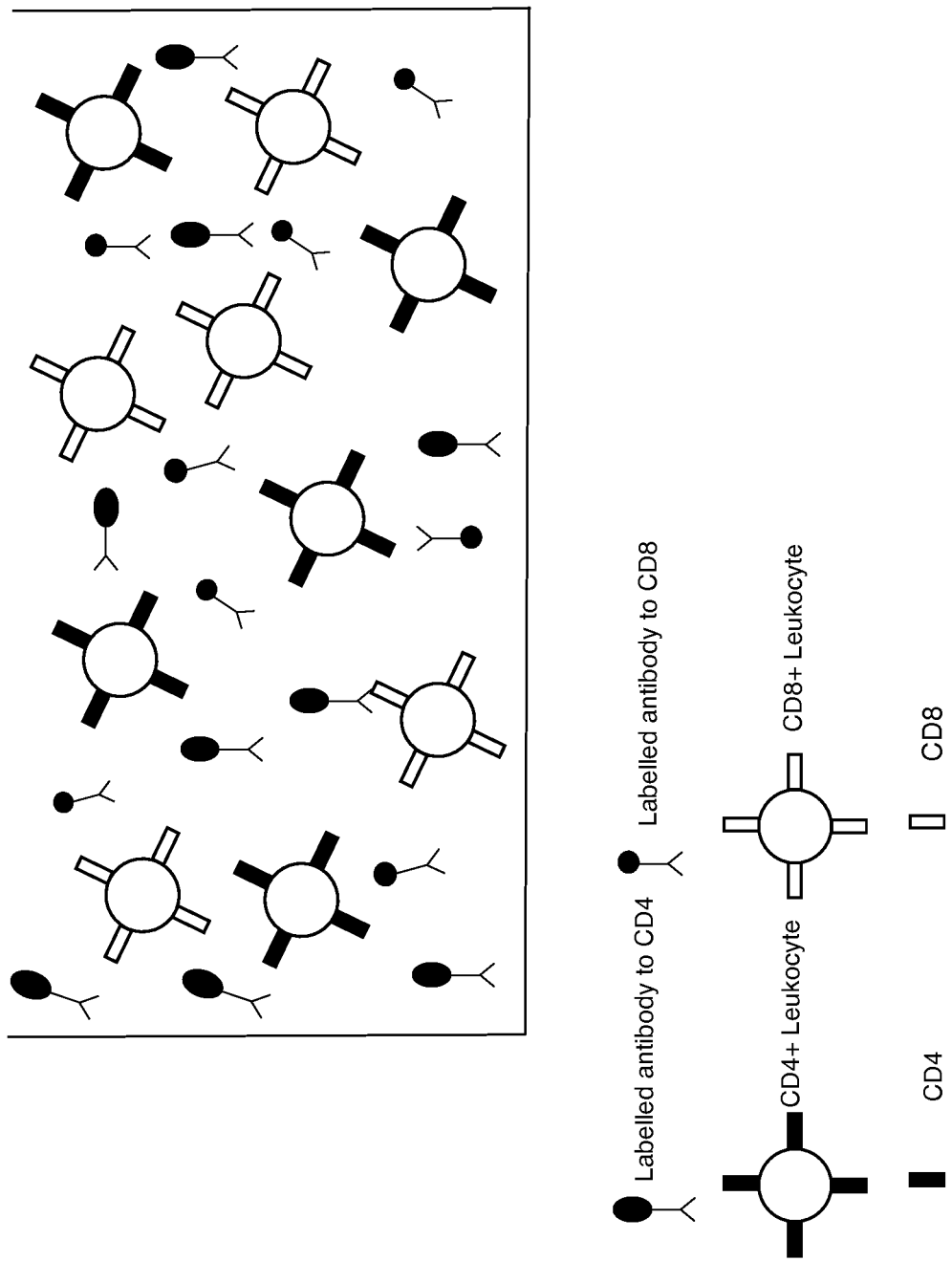
FIG. 2B is a black and white reproduction of the colour representation in FIG. 2A.
Figure 3A:
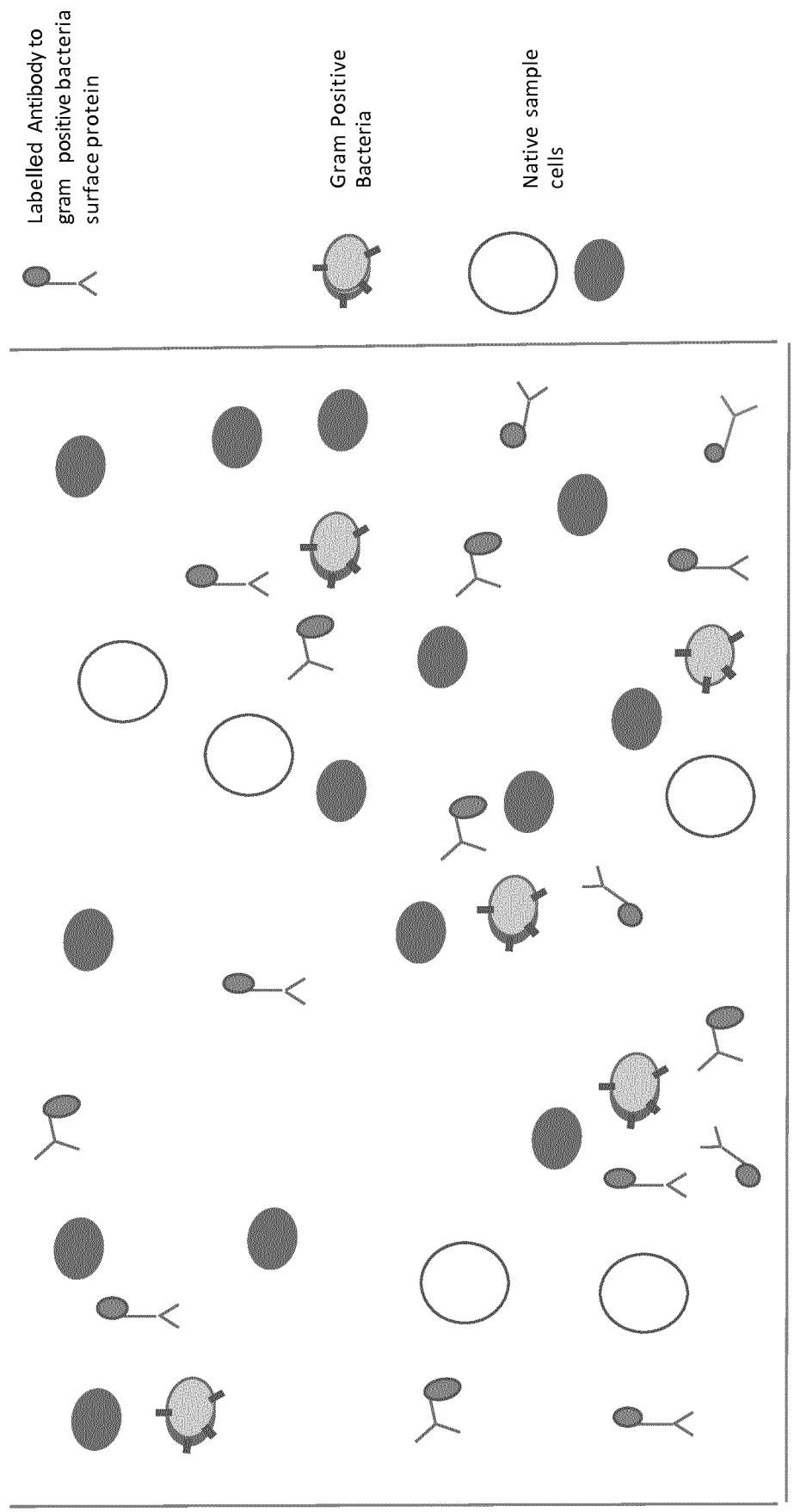
FIG. 3A is a diagrammatic representation of an another embodiment of a method for differentiating and/or identifying cells or other components in a biological sample which uses an antibody to a Gram-positive bacteria surface marker to determine a type of bacterial infection.
Figure 3B:
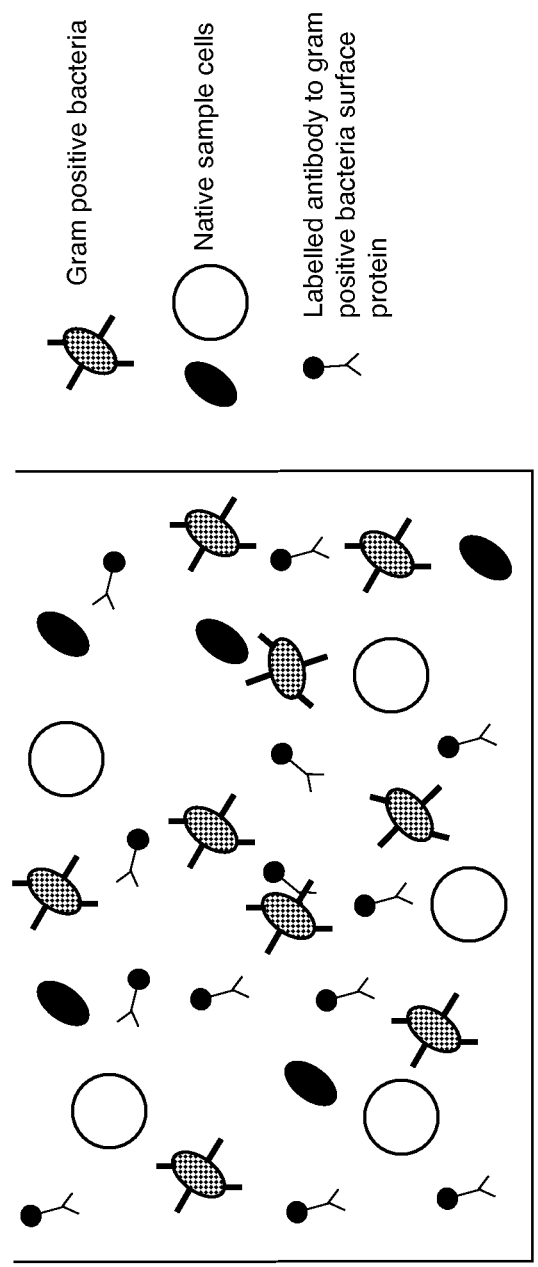
FIG. 3B is a black and white reproduction of the colour representation in FIG. 3A.
Figure 4A:
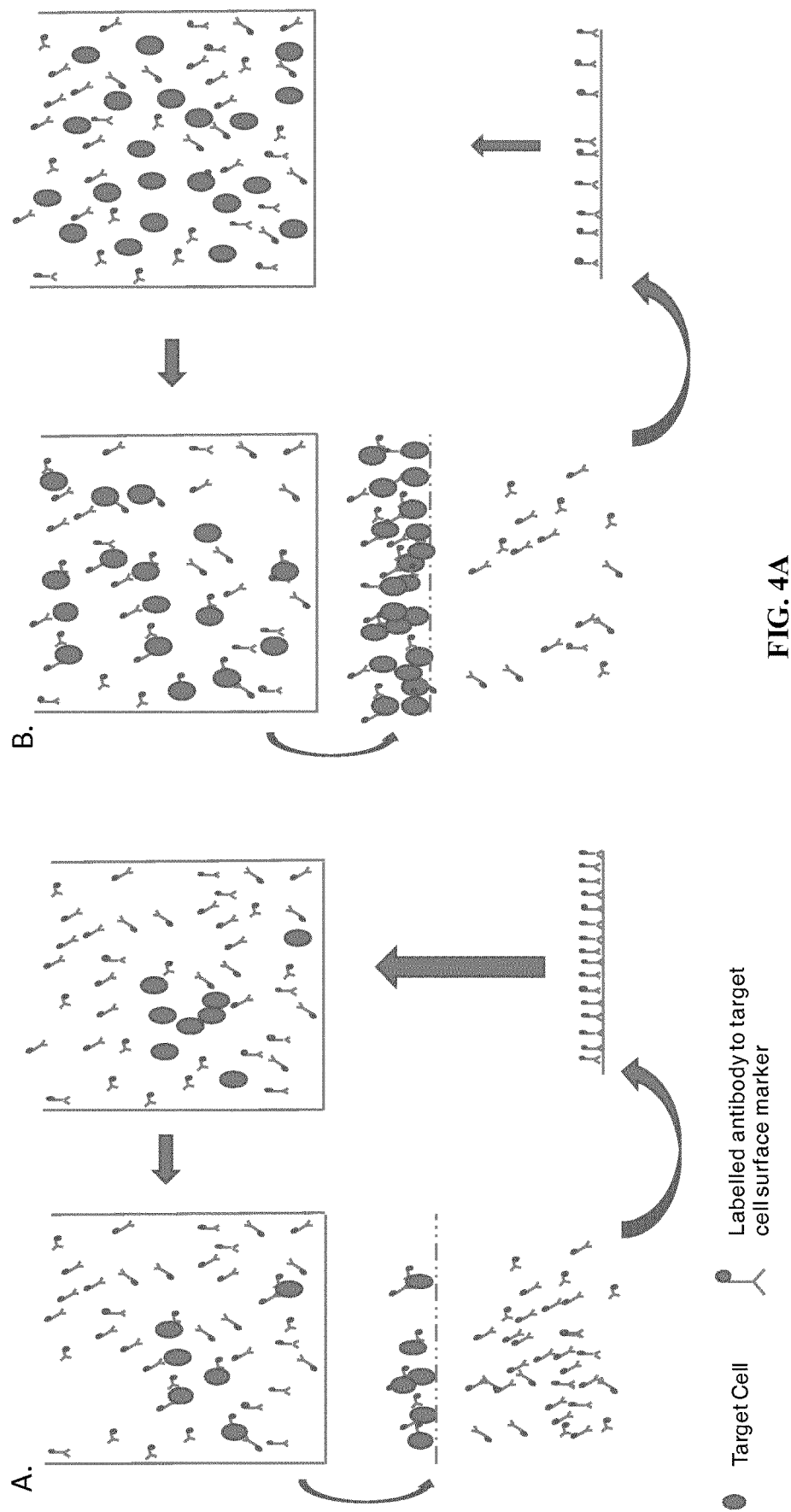
FIG. 4A is a diagrammatic representation of how the number of cells in a sample affect the final signal strength.
Figure 4B:
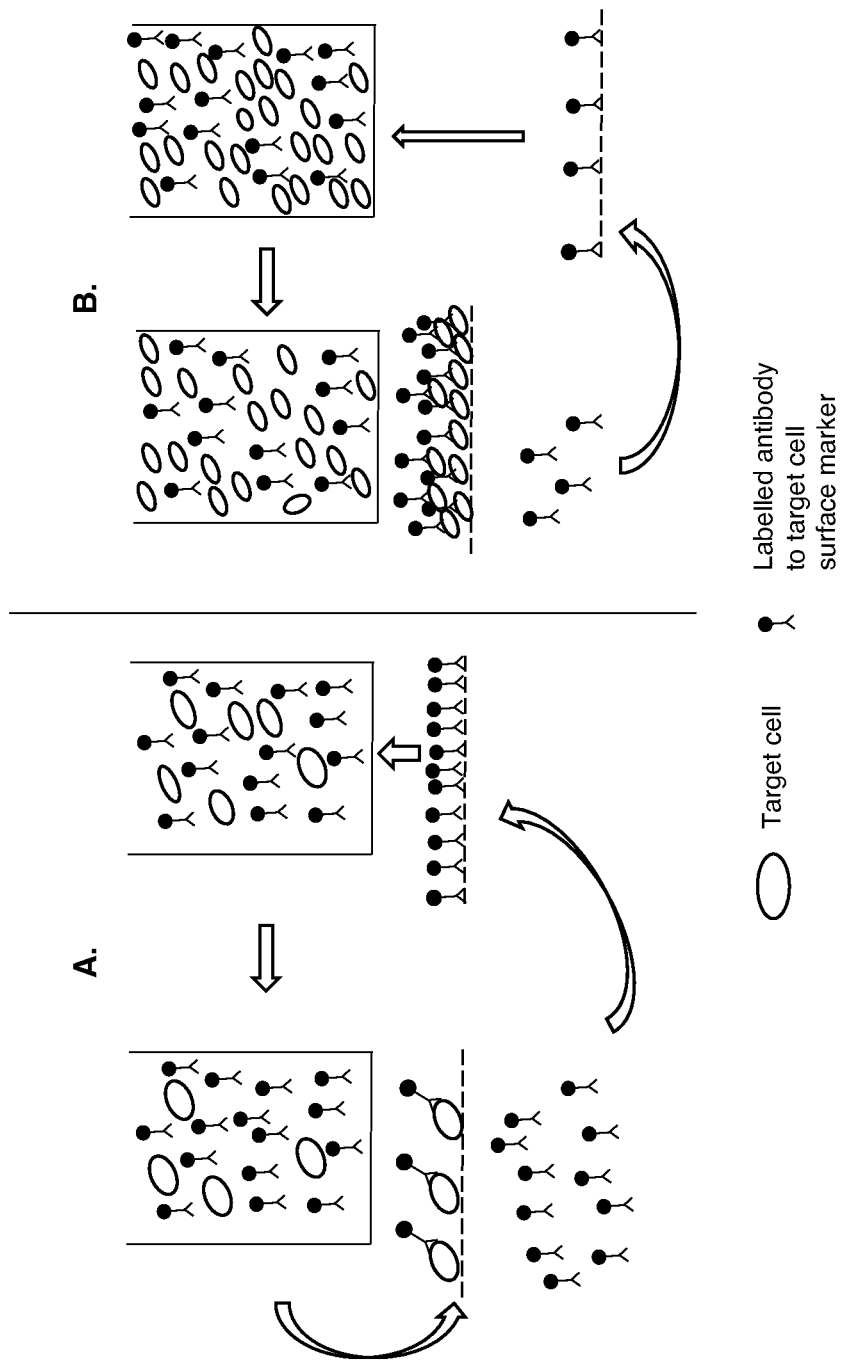
FIG. 4B is a black and white reproduction of the colour representation in FIG. 4A.

FIGS. 2(A and B) shows a more particular example, which uses antibodies to CD4 and CD8 to determine CD4+: CD8+ ratios in a sample to assess HIV progression. FIGS. 3(A and B) shows another example, which uses an antibody to Gram-positive bacteria surface marker to determine a type of bacterial infection. FIGS. 4(A and B) shows how the number of cells in the sample affect the final signal strength. Panel A of each of FIGS. 4A and 4B shows that when there is a low number of target cells in the sample, this leads to a small loss of antibodies in the filtrate and therefore a high signal. Panel B shows that when there is a high number of target cells in a sample, this lead to a high loss of antibodies in the filtrate and thus a low signal. As can be seen from FIGS. 4A and B collectively, the higher the number of target cell in the sample, the higher the number of antibodies that are removed at the filtration stage, and thus a lower signal will be produced.

The system for differentiating and/or identifying cells includes three mam components: a sampling module for receiving and incubating samples with antibodies, a filter for filtering the sample and an analyser for analysis of the filtrate. The analyser may include one or more sensors operatively coupled to a computing device such as a personal computer, laptop computer, server or the like. The computing device includes at least one processor and at least one memory, which stores processor-executable instructions. When these instructions are implemented by the processor, it implements one or more steps of the methods as described herein.

According to some embodiments of this disclosure, the filter may include a membrane with a pore size less than 2 micrometres to remove all the cells or substantially all the cells from a sample and more preferably, a blood sample. In other embodiments, a magnetic separation system can be used instead of the filter or any other apparatus of removing the cells along with marker-bound antibodies from the blood sample. In other embodiments, the cells may be removed through sedimentation, centrifugation, or through the use of antibodies to immobilize, or remove the target cells.

According to some embodiments of this disclosure, either the unbound antibodies remaining in the filtrate or the antibodies bound to the cells, either when bound or by after treatment to unbind them from the cell surface, may be conjugated to one or more molecules that would facilitate further analysis such as a reporter. The conjugated molecules may include enzymes, such as horse radish peroxidase, which can catalyse a measurable change in a developer fluid. In other embodiments, the conjugated molecules may include a fluorescent probe, which can be measured through light emission. In yet other embodiments, the conjugated molecules may include biotin, to which a further reporter molecule can be attached though a high affinity binding process using a biotin-streptavidin/biotin/avidin system. In some embodiments, unconjugated antibodies can be used. In yet more embodiments, a secondary reporter can be applied. For example, a secondary antibody labelled with an enzyme or reporter molecule is utilized in case of the use of unconjugated antibodies.

The term "reporter" means a molecule, which, by its chemical nature, provides an analytically identifiable signal that allows the detection of a predetermined antigen. Detection may be either qualitative or quantitative. Some examples of reporters include enzymes, fluorophores, gold or radionuclide containing molecules (i.e., radioisotopes). In the case of enzyme immunoassay, an enzyme is conjugated to the second or third immunoglobulin, generally by means of glutaraldehyde or periodate. Other types of enzymes that can be used includes horseradish peroxidase, glucose oxidase, -galactosidase, and/or alkaline phosphatase.

In some embodiments of the present disclosure, a whole blood sample is incubated with a mixture of a predetermined amount of labelled antibodies against a range of surface markers to identify, for example, red blood cells, platelets, and/or to differentiate white blood cells. The blood sample can be further incubated to allow the antibodies to bind to surface antigens. In other embodiments, a particular fraction of whole blood may be analysed, such as separated white blood cells.

In some embodiments of the present disclosure, the system may include a structure containing discrete regions to which surface markers, against which the antibodies have been raised, are bound. A non-limiting example of such a structure is a structure made from a suitable plastics material such as microtiter plate or a cuvette. In this case, the filtrate can be incubated inside the structure allowing the remaining antibodies, those that have not bound to the cells prior to the filtration, to bind to immobilized surface markers. Following the incubation, the structure can be washed to remove all unbound components of the filtrate. If unconjugated antibodies are utilized, a further incubation with a solution containing a secondary reporter molecule (e.g., a labelled secondary antibody, streptavidin-conjugated enzyme, or probe) may be required. If an enzyme, such as horseradish peroxidase (HRP), is used as a labelled secondary antibody, a developer solution may be required to pour into the structure. The developer solution may relate to a 3,3',5,5'-Tetramethylbenzidine (TMB), which may undergo a measurable colour change, the rate of which is dependent on the amount of enzyme. Accordingly, the amount of bound antibodies can be determined based on the extent of colour change measured. In other embodiments, developer solutions can include colorimetric, fluorescent, and/or chemiluminescent solutions.

As discussed above, the difference in antibody concentrations prior to filtration and after filtration can be used to calculate the concentration and/or ratio of the surface markers in the original blood sample. The concentration and/or ratio of the surface markers, in turn, can serve a basis for calculation of the number of cells of each type, including differentiated white blood cells.

In yet another embodiment of the present technology, antibodies to pathogen surface markers are used to identify and quantify pathogens in a sample. In still another embodiment of this disclosure, surface markers to mycoplasma cells can be used to detect mycoplasma growth in cell lines.

In some embodiments of the present disclosure, the system for identifying cells in a blood sample may include a biosensor. The biosensor is an analytical device that can be used for the analysis of analyte. The biosensor may comprise a sensitive biological element (e.g., tissue, microorganisms, organelles, cell receptors, enzymes, antibodies, nucleic acids, whole blood or a fraction thereof etc.), a biologically derived material or biomimetic component that interacts with the analyte under study. The biologically sensitive elements can also be created by biological engineering. The biosensor further comprises a transducer or a detector (e.g., a physicochemical, optical, piezoelectric, or electrochemical device) that transforms a signal resulting from an interaction of the analyte with the biological element into another signal that can be more easily measured and quantified. The biosensor further comprises a biosensor reader device with associated electronics (e.g., a computing device) that are primarily responsible for the display of the results in a user-friendly way.

In some embodiments, this technology may be incorporated into a membrane based device using a colour reporting method, such as colloidal gold, to provide rapid measurements of the presence or absence of one or more components in a sample, e.g., pathogen, or the levels of one of more elements in a sample, e.g., CD4+ and CD8+ cells (see FIG. 2).

According to various embodiments, the present technology can be also configured to determine diseases of a subject, an individual or an animal, whose samples are preferably, fluid samples were tested and analysed. Moreover, the present technology may provide automatic recommendations, suggestions, or plans for treating identified diseases. Non-limiting examples of treatment modalities include radiotherapy, surgery, chemotherapy, hormone ablation therapy, pro-apoptosis therapy, immunotherapy, phototherapy, cryotherapy, toxin therapy, treatment with an anti-infective drug or pro-apoptosis therapy. One of skill in the art would know that this list is not exhaustive of the types of treatment modalities. Diseases can be determined based on the results of differentiating/identifying of cells in samples as described herein. For example, determination of white blood cell count using the methods of this disclosure could be used to determine if an individual has an infection leading to treatment with antibiotics. In another embodiment, the determination of red blood cell count using the methods of this disclosure can be used to determine if an individual is anaemic and needs to be treated, for example, with iron supplements. In yet another embodiment, the determination of decreased white or red blood cell count may be a consequence of treatment with certain drugs, for example, clozapine. Therefore, the choice of treatment can also depend on a cell count. Determination of blood cell count and cell count in other biological samples can, therefore, be seen to be very important for treatment decisions in the medical field. In preferred embodiments, the methods described herein further include the step of treating a subject.

The terms "patient," "subject," "host" or "individual" used interchangeably herein, refer to any subject, particularly a vertebrate subject, and even more particularly a mammalian subject, for whom therapy or prophylaxis is desired. The term "subject" is inclusive of a human mammalian subject and a non-human mammalian subject.

As used herein, the terms "treatment," "treating," and the like, refer to obtaining a desired pharmacologic and/or physiologic effect. The effect may be therapeutic in terms of a partial or complete cure for a disease or condition and/or adverse effect attributable to the disease or condition. These terms also cover any treatment of a condition or disease in a mammal, particularly in a human, and include: (a) inhibiting the disease or condition, i.e., arresting its development; or (b) relieving the disease or condition, i.e., causing regression of the disease or condition.

Figure 5A:
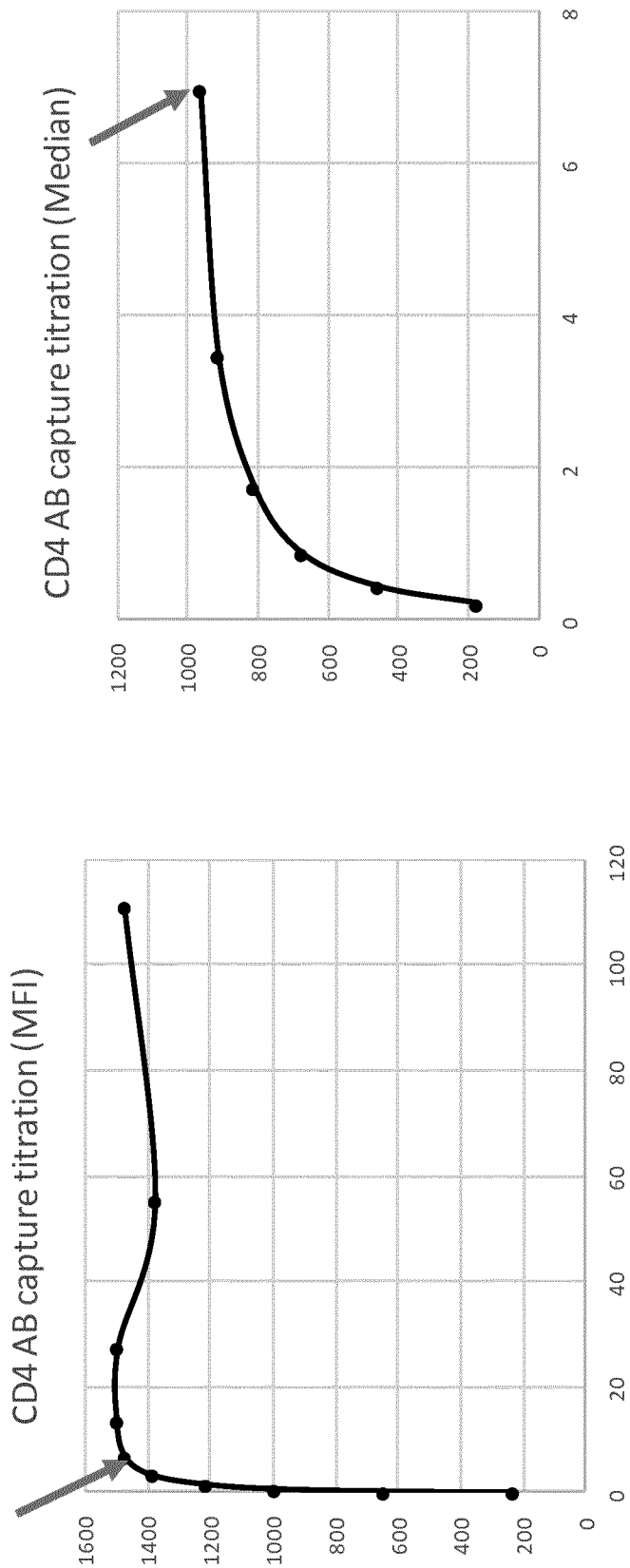
FIG. 5A is a diagrammatic representation a method of the use of an antibody to CD molecules to determine the number of cells in a sample.
Figure 5B:
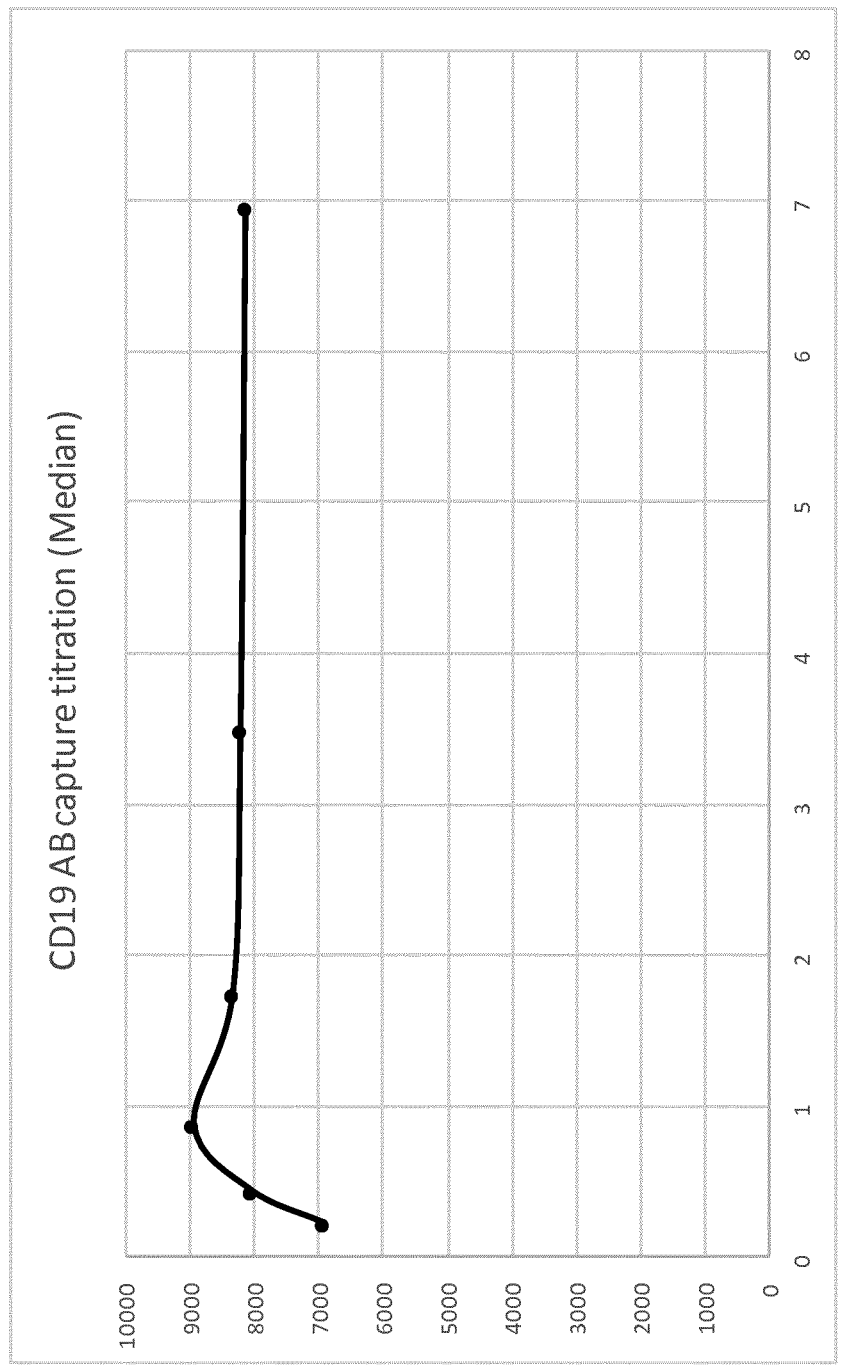
FIG. 5B shows results of using antibodies to CD19, a surface marker not expressed by the VL3 Cell line, to determine if the effect demonstrated in FIG. 5A could be due to non-specific binding of the antibodies to the cells, or antibody aggregation. The Y-axis is fluorescence; the X-axis is cell count (reciprocal)=1/(cell count×10e6).

The use of an antibody to CD molecules to determine the number of cells in a sample is shown in FIG. 5A and 5B. A VL3 cell line with stable expression of CD surface markers was used for the experiment. Fluorescently labelled anti-CD4 antibodies at a concentration of 0.0008 mg/ml were incubated with samples of cells at a range of cell concentrations, from $4.6 \times 10e6$, to $0.009 \times 10e6$ cells per ml. Following incubation to allow the antibodies to bind to the CD4 molecules on the surface of the cells, the samples were centrifuged to remove the cells. The supernatant was removed and the amount of antibody remaining in the supernatant was assayed. This was done by adding antibody-binding beads to the supernatant and incubating to allow the remaining antibodies to bind to the beads. The beads were then run through a BD FACSDiva flow cytometer to measure the fluorescence. As shown in FIG. 5A there was a clear inverse relationship between the number of antibodies present in the supernatant, and the number concentration of cells in the sample. Beyond the lower limit of $1.4 \times 10e5$ cells per ml (shown by arrow), the number of cells could not be determined in this experiment.

The process was repeated using antibodies to CD19, a surface marker not expressed by the VL3 Cell line, to determine if this effect could be due to non-specific binding of the antibodies to the cells, or antibody aggregation. Referring to FIG. 5B, there is a small reduction in the signal at very high cell concentrations, but not sufficient to interfere with the result obtained through specific binding of antibodies to expressed CD molecules. This data supports that the method is effective in determining the number of cells expressing a particular marker, present in a sample and the suitability of this method in differentiating and quantifying cells types present in a sample.

Those skilled in the art will appreciate that the present technology allows for identifying cells not only in blood samples, but also any other biological fluids, tissue samples, food, water, and cultured cells. The disclosed technology provides a fast and accurate low cost method and system which can be incorporated into a portable and/or disposable unit to provide a fast, field/point-of-care-based method applicable for blood cell count and differentiation for diagnostics, health monitoring, blood typing and monitoring of HIV progression, distinguishing between infections of viral or bacterial origin, pathogen detection and identification, diagnostics based on biological fluid and tissue samples, utilization in food industry, agricultural applications, veterinary applications, water quality testing, and/or detecting mycoplasma contamination in cultured cell lines.

It will be appreciated that the biological material may be an isolated biological material that may or may not be purified. By "isolated" is meant material that is substantially or essentially free from components that normally accompany it in its native state, or from components present during its production when purified or produced by synthetic means. Thus, the term "isolated" also includes within its scope purified or synthetic material. As used herein, the term "purified" refers to material (e.g., a blood sample, a fluid sample) that is substantially free of cellular components or other contaminating material from the source from which the material is derived. "Substantially free" means that a preparation of a material is at least 10%, 20%, 30%, 40%, 50%, 60%, 70%, 80%, 90%, 95%, 96%, 97%, 98%, 99% pure.

Method and System for Controlling Dynamic Range of Assay Quantification for Analyte Detection The present technology also provides for an assay analysis based on immunoassay methods, where a concentration of analyte in a sample is determined in reliance to intensity of detection signal. These methods are generally applicable for detection and/or quantification of analytes such as an antigen, antibody, protein, and nucleic acids in samples such as biological fluids (e.g., blood) or non-biological fluids. The samples may be isolated and may or may not be purified.

The term "assay," as used herein, refers to an analytical detection method including, but not limited to, enzyme-linked immunosorbent assay (ELISA), radioimmunoassay (RIA), chemiluminescent assay, bioluminescent assay, fluoroimmunoassay, protein microarray, DNA microarray, RNA microarray, and/or protein biochip assay.

The term "target analyte," as used herein, refers to a biochemical substance to be detected or quantified in a biological sample and may comprise one or more of the following: an antigen, antibody, protein, lipid, carbohydrate, and nucleic acids, and any combinations thereof.

The term "solid phase," as used herein, refers to planar or nonplanar solid support surfaces used in immunodetection methods and may comprise one or more of the following: a polystyrene microtiter plate, a microsphere, a bead, a membrane, a polymer, copolymer, a cross-linked polymer, and the like.

The term "binding reagent," as used herein, refers to a biochemical substance capable of reacting with the target analyte or used for detecting the presence of the target analyte in a sample. The binding reagent may refer to an antigen, an antibody, a protein, and/or an oligonucleotide.

The term "detection signal" or simply "signal," as used herein, refers to a measurable signal produced by a labelled analyte or conjugated analyte or labelled binding reagent or conjugated binding reagent. The detection signal may be measured using, for example, one or more of the following methods: a photometric method, spectrophotometric method, radiometric method, and fluorometric method. Those skilled in the art will appreciate that other methods, such as mass spectrometry, can be also used for measuring the detection signal.

A dynamic range (or "detection range") of assay results (signals) can be defined as the lowest concentration to the highest concentration of an analyte (also referred herein to as "target analyte") that can be accurately detected by the assay. The concentration of the analyte is generally required to be present within the dynamic range or detection range of the assay in order to be measured. The dynamic range of assay results can be predetermined or dynamically changed.

Generally, the present technology relates to a method for quantitative detection of one or more target analytes by controlling the dynamic range of an assay. The method comprises the following steps: i) providing the one or more target analytes in the biological sample; ii) contacting the one or more target analytes with a mixture of at least one conjugated binding reagent and at least one unconjugated binding reagent, wherein the at least one conjugated binding reagent and the at least one unconjugated binding reagent are specific to the one or more target analytes; iii) measuring the interaction between the one or more target analytes and the mixture of the at least one conjugated binding reagent and the at least one unconjugated binding reagent; and iv) controlling a dynamic range of assay signals by adjusting a ratio of the at least one conjugated binding reagent and the at least one unconjugated binding reagent in the mixture.

The term "ratio" refers to a ratio in the standard sense; the amount of one element relative to the amount of another another element. This could be expressed by molarity, weight or volume. Preferably, the ratio is selected from the group consisting of a molar ratio, a weight ratio and a volumetric ratio, and any combination thereof. In preferred embodiments, the ratio is a molar ratio. In other preferred embodiments, the ratio is a volumetric ratio. In yet other preferred embodiments the ratio is a weight ratio.

It should be clear that the above method may have more limiting example implementations as discussed below. In some embodiments, the method is focused on providing a conjugated agent and an unconjugated agent in a sample with target analytes so that these agents compete with each other to bind to the analyte. Accordingly, providing the conjugated and unconjugated agents can reduce assay signals, thereby changing a dynamic range.

In other embodiments, the method is focused on using conjugated or unconjugated analytes, which are added to a sample to dilute the target analytes, which ultimately leads to the change of the assay signal. For example, the conjugated analyte could bind to an antibody bound to a solid phase, which has a fluorophore that is quenched by binding to the conjugated analyte. By having conjugated and unconjugated analytes, the amount of quenching for a given concentration or amount of analytes can be reduced, thereby changing the dynamic range.

Alternatively, in other embodiments, only one or more conjugated analytes and a binding reagent specific to the one or more target analytes is needed. The conjugated analytes are bound with a marker that is modified or otherwise activated or deactivated as binding takes place increasing or decreasing a signal (such as fluorescence) from the conjugated analyte. As the conjugated analytes bind to the reagent, the signal from the conjugated analytes increases or decreases. The ratio between conjugated analyte and unconjugated analyte (in the sample and possibly with addition of additional unconjugated analyte as well) determines the magnitude of the increase or decrease in the signal.

In other embodiments, rather than conjugated analyte, one or more modified analytes (which could be simply a molecule containing some of the same structures as the target analyte) could be used. Both modified analytes and target analytes (from the sample with or without addition of regular analyte) bind to the one or more first reagents. One or more secondary conjugated reagents can then be added, each of which binds only to either one or more of the target analytes or one or more of the modified analytes. The ratio between modified analyte and target analyte determines the magnitude of the increase or decrease in the signal. In some embodiments, the one or more modified analytes are molecules, which contain structures that are the same as structures within the target analytes, for example, at least some of the modified analytes may be or include a subunit of at least one of the target analytes. In some embodiments, the target analyte could be a protein. In some embodiments, the first reagent could be an antibody, which binds to both the target analyte and modified analyte conjugated reagent, whilst the second conjugated reagent is an antibody, which binds only to the target analyte, but not the modified analyte. In some embodiments, the conjugated reagent is conjugated with a fluorophore for fluorescent detection.

In other embodiments, there are one or more target analytes and one or more modified analytes, which compete to bind to a conjugated reagent. Only binding of either target analyte or modified analyte causes the activation or deactivation of the conjugated marker (e.g., quenching of a fluorophore). Hence, the ratio between the modified analyte and target analyte determines the magnitude of the increase or decrease in the signal.

The term "conjugated," as used herein, means connected with a marker that leads to a signal measurable with a sensor whether a direct signal producing marker (such as a fluorophore) or a chemical group, which can be used to attach a signal producing group such as a biotin or streptavidin group.

It should be noted that binding of an analyte to a reagent prevents or reduces the number of analytes that can bind to that reagent so the analytes compete to bind to a particular reagent.

Figure 6A:
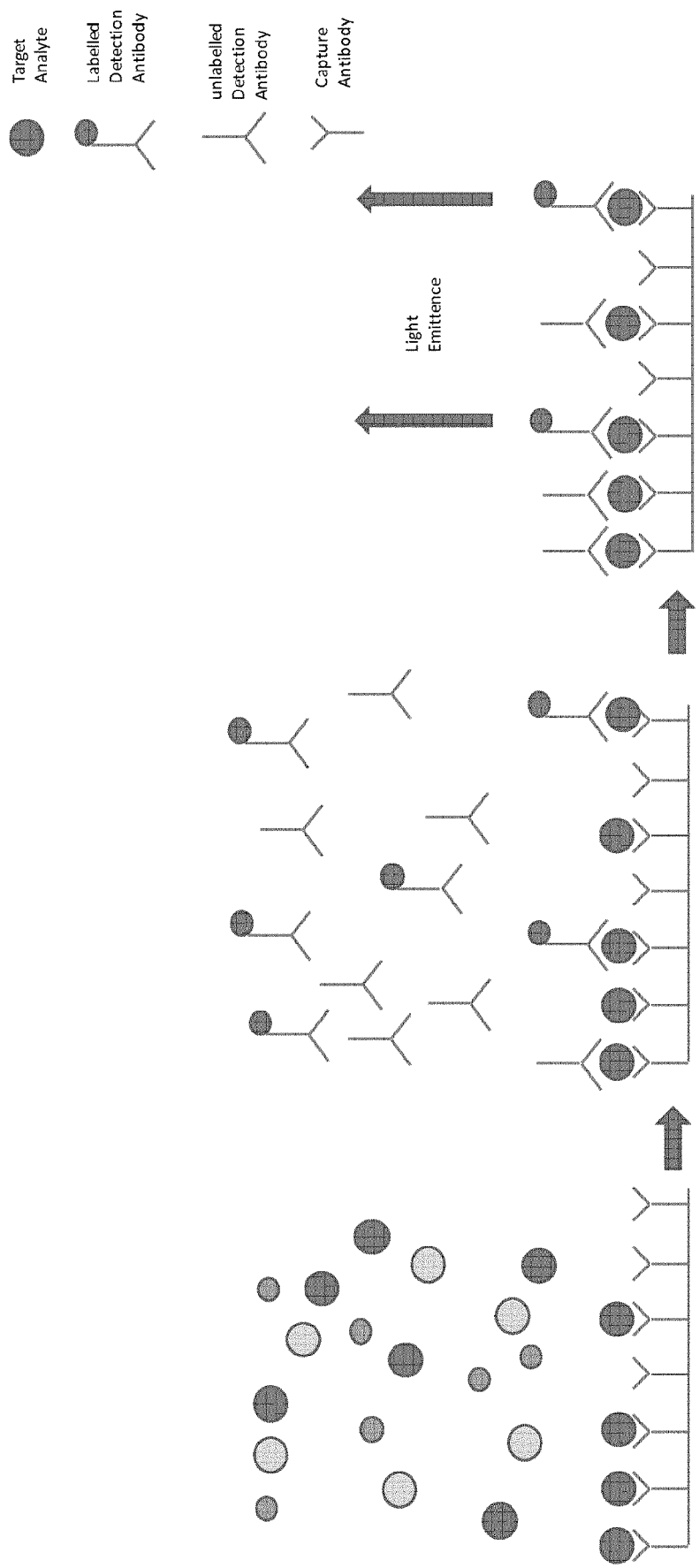
FIG. 6A is a diagrammatic representation of a method for quantitative detection of one or more target analytes by controlling the dynamic range of an assay according to an embodiment.
Figure 6B:
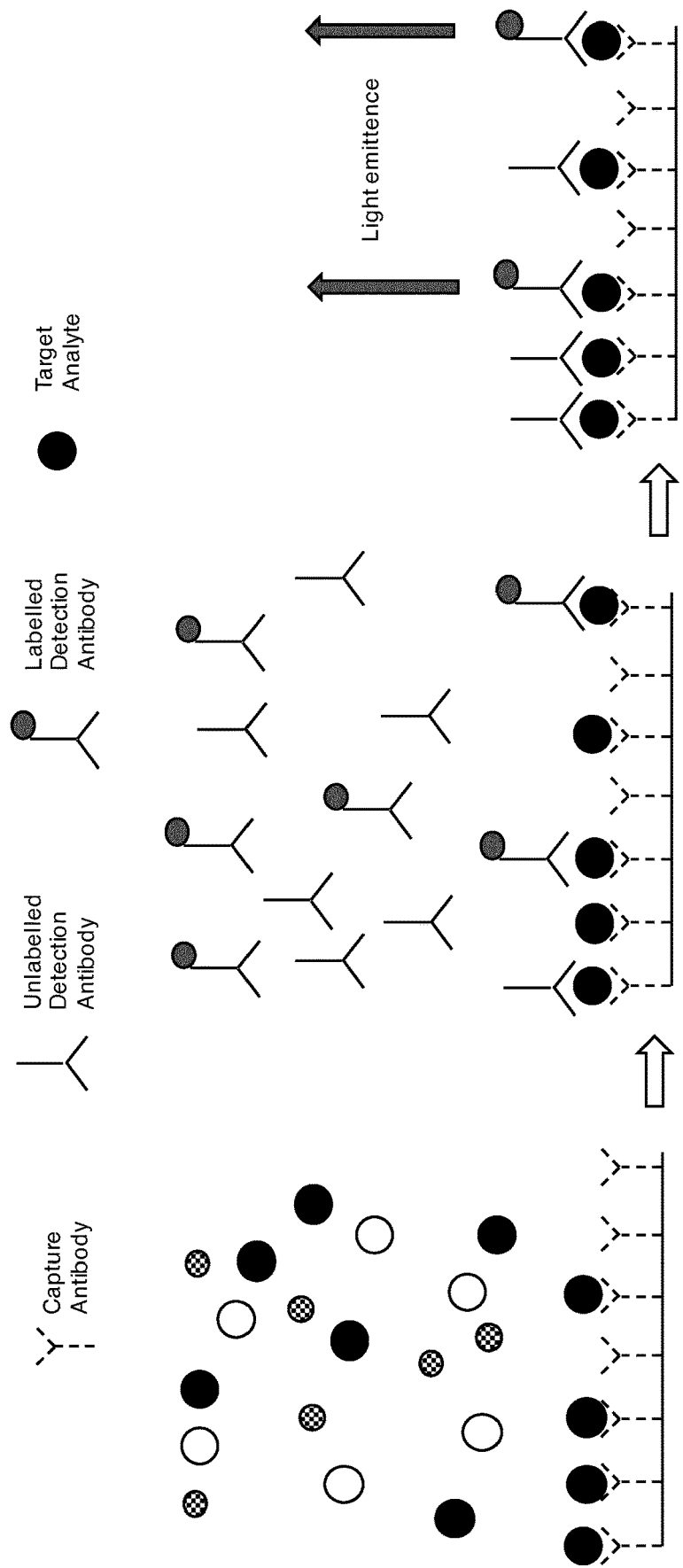
FIG. 6B is a black and white reproduction of the colour representation in FIG. 6A.

In an embodiment, the present technology may include the following example method for quantitative detection of one or more target analytes by controlling the dynamic range of an assay. The method comprises the steps of: i) providing a solid phase immobilized with the one or more molecules, which bind specifically to the target analytes; ii) contacting the solid phase with the sample, in which the concentration or presence of the one or more target analytes is to be measured; iii) introducing a binding reagent, which will contain a mixture of reagents, which will be either conjugated or unconjugated to a reporter molecule, such as a fluorophore; iv) allowing to compete the conjugated and unconjugated binding reagents in order to bind to the immobilized target analyte. The amount of fluorophore can be measured by detecting light emission. Further, the concentration of target analyte can be calculated based on these measurements. The method may further include the steps of: v) controlling a signal level (and thus dynamic range) through adjustment of the ratio of conjugated and unconjugated binding reagents. This process is further illustrated in FIG. 6. Specifically, FIG. 6 shows a sandwich ELISA using 4:6 ratio of fluorophore conjugated:unconjugated detection antibody to lower the signal produced.

In one or more embodiments, the conjugated binding reagent or the unconjugated binding reagent includes an antibody, an antigen, an aptamer, a protein, and/or an oligonucleotide. In certain embodiments, the conjugated binding reagent includes a binding reagent coupled with a conjugate selected from a group consisting: an enzyme, a protein, a fluorophore, a streptavidin, an avidin, an antibody, an antigen, an aptamer, and an oligonucleotide. In certain embodiments, the conjugated binding reagent is conjugated to a label, which allows detecting the conjugated binding reagent bound to a target analyte. Labels may include enzymes capable of producing a measurable response (e.g., visible colour change) in the presence of corresponding substrates. The enzymes may include, but not limited to, horseradish peroxidase (HRP), alkaline phosphatase (AP), luciferase, beta-galactosidase, and glucose oxidase. Labels or conjugates used for detection of binding reagents may also comprise carrier molecules such as a fluorophore, streptavidin, and avidin. Other example labels could be also used to allow detection of an electronic or radiographic signal. In various embodiments, target analytes include one or more of the following: an antigen, an antibody, a nucleic acid, a carbohydrate, a lipid, a protein, a polymer, and any combinations thereof.

Figure 8:
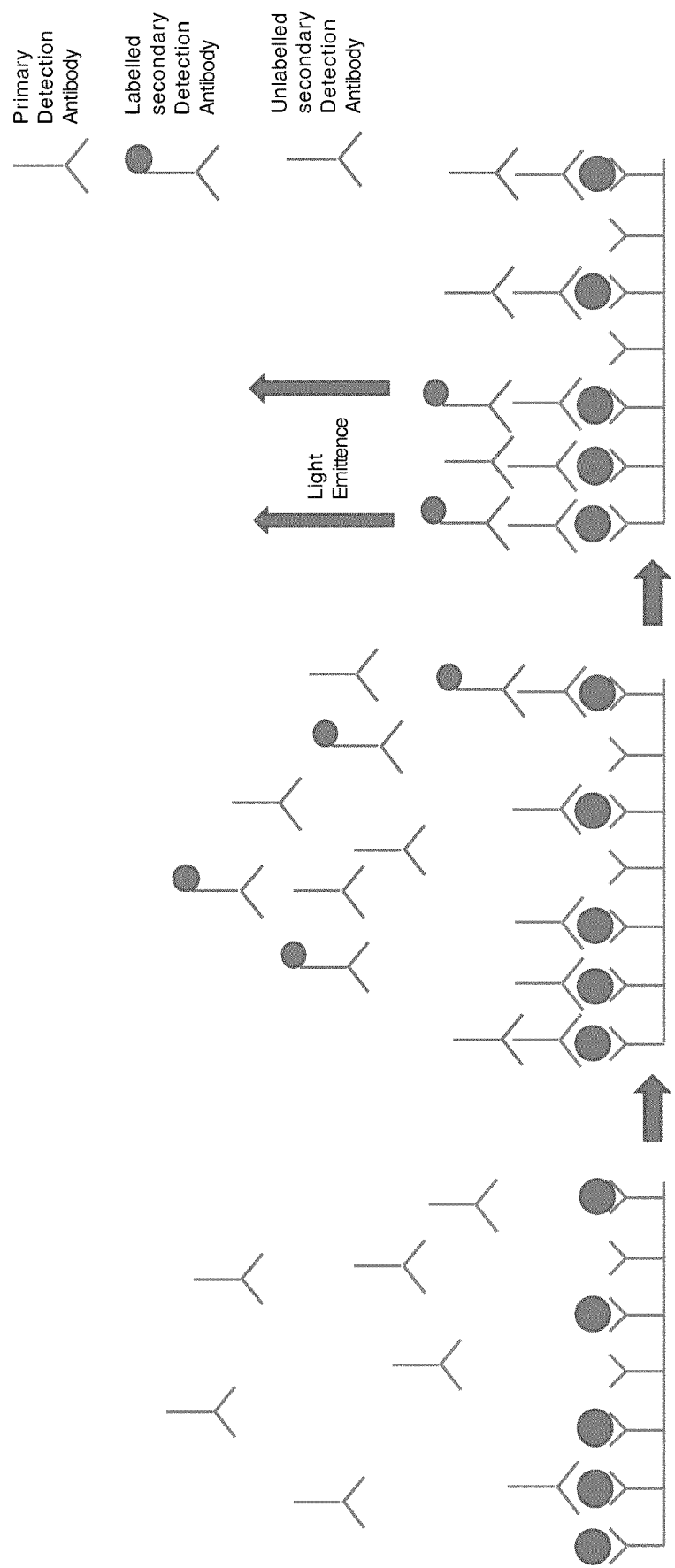
FIG. 8 is an example method for quantitative detection of one or more target analytes by controlling the dynamic range of an assay which uses an unlabelled primary detection antibody with a mixture of labelled and unlabelled secondary detection antibody.

In an embodiment, the binding reagent may comprise a primary binding molecule that directly binds to an analyte such as a primary antibody. In another embodiment, the binding reagent may comprise a secondary binding molecule that binds to a primary binding molecule such as a secondary antibody. This embodiment is further illustrated by FIG. 8 that shows an example method, which uses an unlabelled primary detection antibody with a mixture of labelled and unlabelled secondary detection antibody.

Figure 7A:
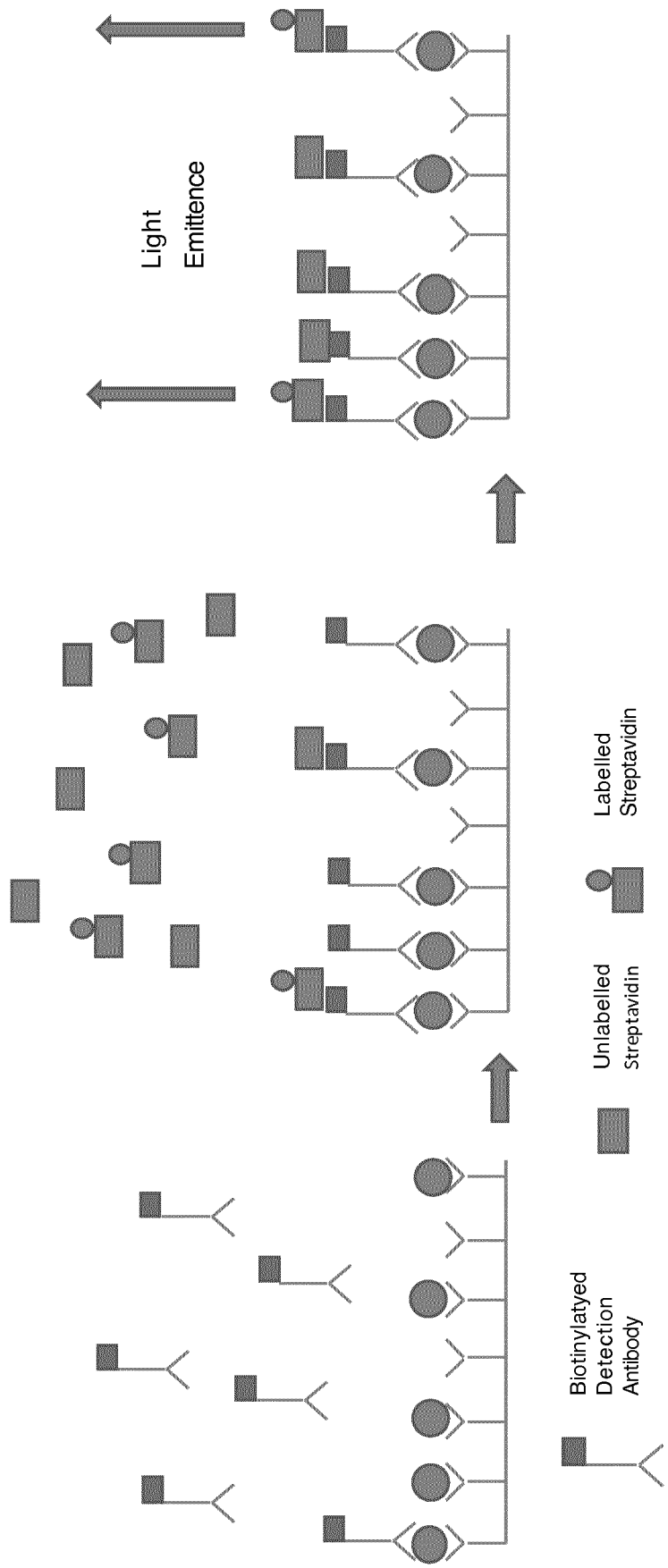
FIG. 7A is a diagrammatic representation of a method for quantitative detection of one or more target analytes by controlling the dynamic range of an assay which uses 100% biotinylated detection antibody with a controlled ratio of labelled and unlabelled streptavidin.

In yet another embodiment, the binding reagent is capable of reacting with another element allowing measurement in the assay. For example, the use of a biotinylated antibody that binds to streptavidin conjugated to an element allows the measurement. This embodiment is further illustrated generally by FIG. 7. FIG. 7A that shows an example method, which uses 100% biotinylated detection antibody with a controlled ratio of labelled and unlabelled streptavidin. The mix of HRP-conjugated and unconjugated streptavidin to control assay range is described below and shown in FIG. 7B and 7C. The purpose of this experiment was to demonstrate that the signal, and therefore assay range can be modified by mixing the HRP-conjugated streptavidin with unconjugated streptavidin, which will compete for binding with the HRP-conjugated streptavidin to the biotinylated detection antibody. And to lower the signal produced, while maintaining the standard curve. The range of target concentrations was run using a range of streptavidin:HRP-streptavidin ratios.

A standard ELISA was performed using Human Prolactin across a wide range of concentration levels, from 49 pg/ml to 5 ug/ml. The assay was performed using a capture antibody coated plate, recombinant prolactin as a target, biotinylated detection antibody, HRP-conjugated streptavidin and TMB as a developer fluid, stopped with 2M $H_2SO_4$. A standard protocol was used as follows: The plate was coated with a capture antibody and subsequently washed with a phosphate buffered saline—Tween 20 solution (PBST). The plate incubated for 2 hours with target in 1% BSA and washed with PBST. The plate incubated for 1 hour with a biotinylated detection antibody and washed with PBST. The plate incubated with HRP-conjugated streptavidin (with a range on unconjugated streptavidin added), followed with a wash step with PBST (as above). The chromogenic substrate 3,3',5,5'-Tetramethylbenzidine (TMB) was added, the reaction stopped after 10 minutes with 2M $H_2SO_4$ and the absorbance read at 450 nm.

Figure 7C:
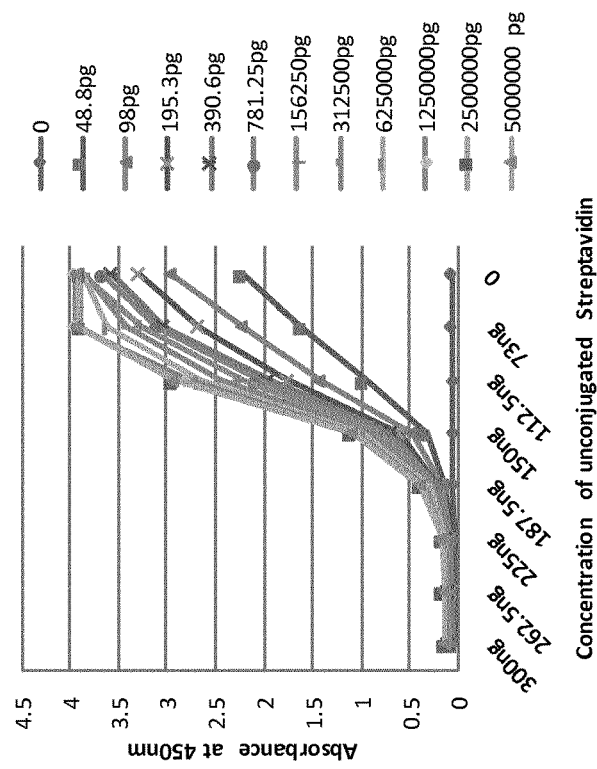
FIG. 7C shows the results of prolactin sandwich ELISA using a range of unconjugated streptavidin mixed with a horseradish peroxidase (HRP)-conjugated streptavidin of FIG. 7B wherein the concentration of unconjugated streptavidin (X-axis) is plotted against the absorbance at 450 nm (Y-axis).
Figure 7B:
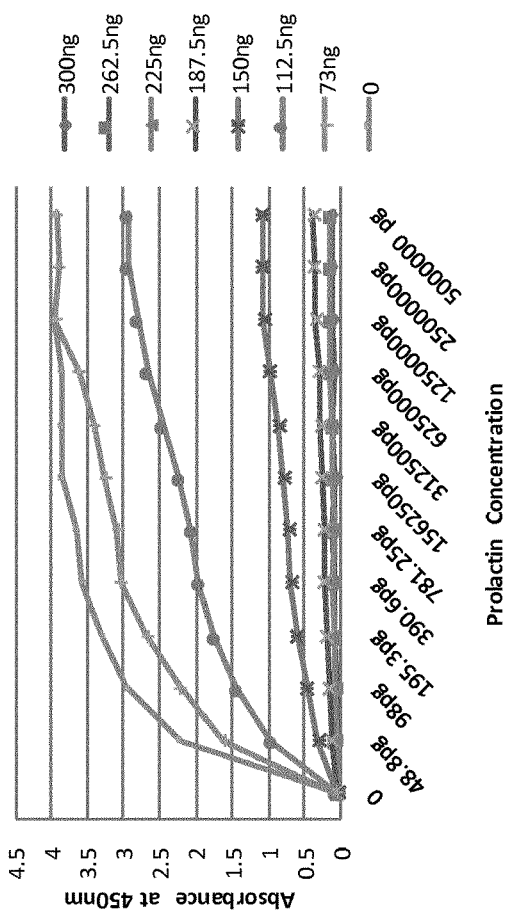
FIG. 7B shows a method for quantitative detection by controlling the dynamic range of an assay by using biotinylated detection antibody with a controlled ratio of labelled and unlabelled streptavidin wherein a prolactin sandwich ELISA using a range of unconjugated streptavidin mixed with a horseradish peroxidase (HRP)-conjugated streptavidin was undertaken.

The data shows that as that as the amount of unconjugated streptavidin is increased, the signal level is reduced. As shown in FIG. 7B, with 0 unconjugated streptavidin, the curve levels off with a prolactin concentration of 1.56 ng, and only concentrations below this can be differentiated. With the addition of 73 ng/ml of unconjugated streptavidin, the signal is reduced and the flattening of the curve does not occur until the prolactin concentration reaches 1.25 ug, all concentrations below can now be differentiated. As the amount of unconjugated streptavidin is increased, the signal level is further reduced, delaying the plateau, and thus increasing the concentration of target that can be determined by the assay. When the concentration of unconjugated streptavidin is increased to 225 ng/ml the development appears to have been completely prevented, indicating that insufficient HRP-conjugated streptavidin has been able to bind to the biotinylated detection antibody. By plotting each target concentration against the concentration of unconjugated streptavidin used, the amount of unconjugated streptavidin needed to adjust the assay range for a particular target can be determined (FIG. 7C).

Figure 9:
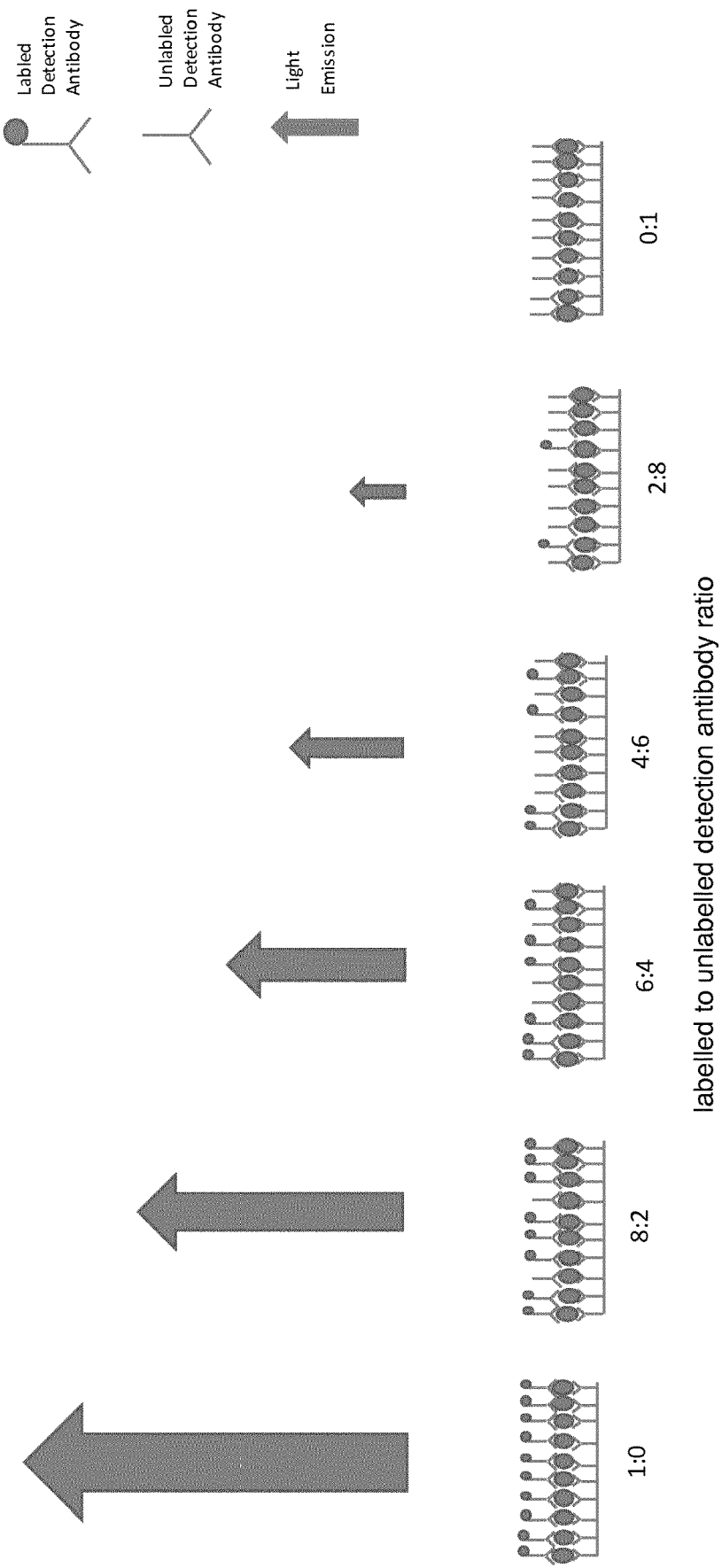
FIG. 9 is a diagrammatic representation of a method of the present technology by which the adjustment of labelled: unlabelled binding reagent ratio adjusts the signal strength. Stated values is the ratio of labelled to unlabelled detection antibody.
Figure 10:
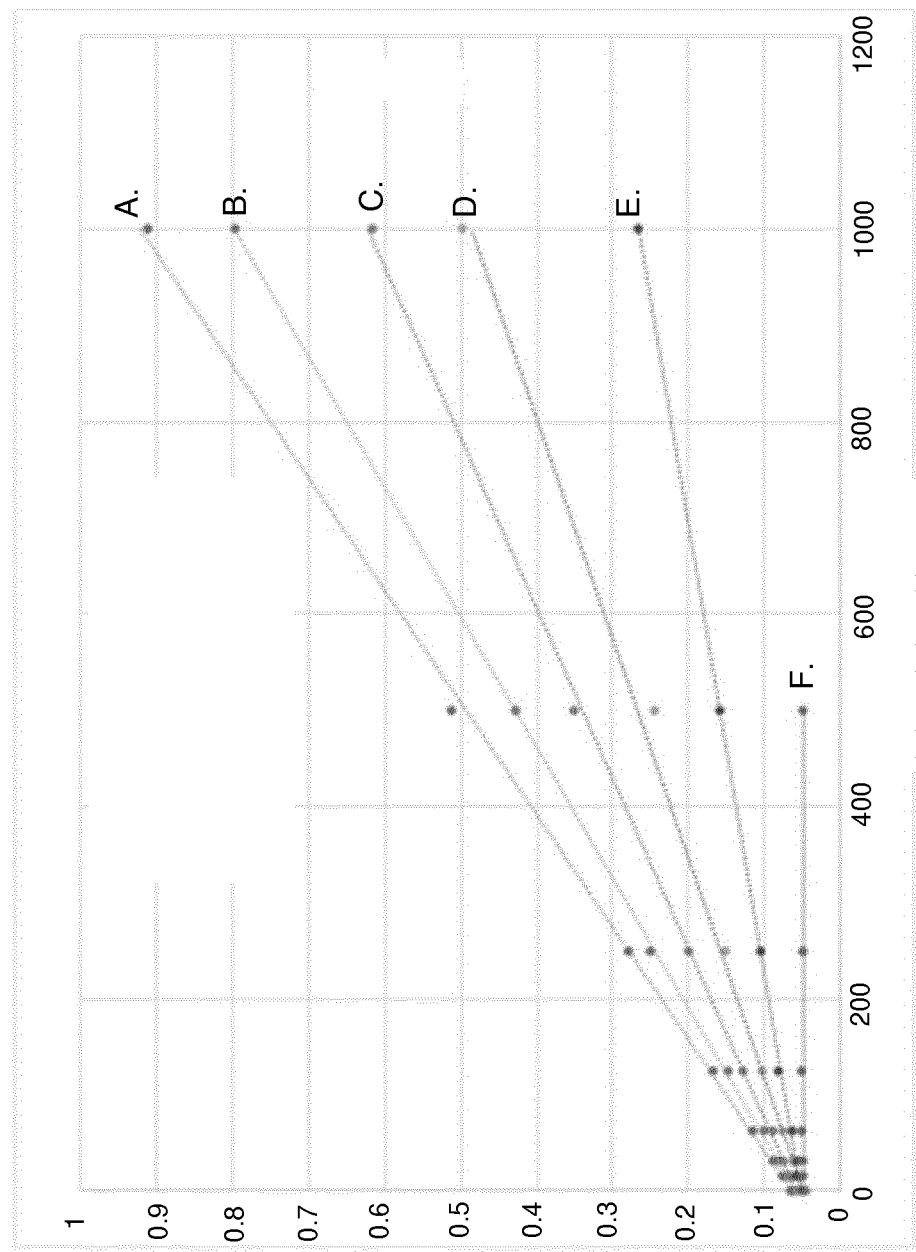
FIG. 10 illustrates experimental results with respect to the process of FIG. 9 and in particular, human prolactin standard curves with adjusted ratios of conjugated:unconjugated detection antibody using HRP-TMB. The X-axis is the human prolactin concentration in pg/mL; the Y-axis is absorbance at 450 nm. Curves A to F are the amount of labelled detection antibody in the antibody mix as follows: A=1; B=0.8; C=0.6; D=0.4; E=0.2; F=0.

As already discussed above, the mixture includes a conjugated binding reagent and an unconjugated binding reagent, specific to one or more predetermined target analytes. Different ratios of conjugated and unconjugated binding reagents in the mixture can be used for precisely controlling the detection range of target analytes immobilized on the solid phase. For example, FIG. 9 shows a process, by which the adjustment of labelled:unlabelled binding reagent ratio adjusts the signal strength. FIG. 10 illustrates experimental results with respect to the process of FIG. 9, which show that the signal strength can be adjusted by changing the ratio of conjugated:unconjugated detection antibody.

The conjugates or labels provide a measurable response or detection signal in the presence of substrate, thereby representing a positive interaction between the binding reagent and target analyte. The detection signal may comprise a colour change, fluorescent signals, and/or chemiluminescent signals, which can be measured by photometric, spectrophotometric or colorimetric methods. The concentration of the target analyte can be accurately determined based on a level of detection signal (e.g., a level of colour change by an enzyme conjugate reflects the concentration of corresponding target analyte).

In an embodiment, the method comprises the use of a binding reagent mixture comprising HRP-conjugated antibody and unconjugated antibody within an immunoassay. The HRP-conjugated antibody competes with the unconjugated antibody for binding sites on a target analyte that is immobilized onto a solid support. The control of HRP-conjugated antibody to unconjugated antibody ratio allows for precise controlling detection signal dampening, which in turn, allows enhancing the dynamic range of the assay in order to cover the concentration range of the target analyte likely to be present in the sample or immobilized to the solid support (see also FIG. 10).

The interaction between the reagent mixture and target analyte includes competitive binding between the conjugated and unconjugated binding reagents to the binding sites on target analytes immobilized on the solid phase (see also FIG. 6).

In yet another exemplary embodiment, the target analyte comprises an antigen immobilized onto a solid phase support. The mixture may include an unconjugated binding reagent having an antibody capable of specifically binding to the immobilized antigen and a conjugated binding reagent having an enzyme-labelled antibody capable of binding to the immobilized antigen. Upon adding the mixture to the solid phase comprising target antigen, the enzyme-labelled antibody competes with the unlabelled antibody for binding sites on the surface of the target antigen.

The concentration of multiple analytes may differ within a biological sample. For example, thyroid-stimulating hormone (TSH) is normally present in the range of pg/ml, while luteinizing hormone (LH) and follicle-stimulating hormone (FSH) are present in the range of ng/ml, in a biological sample. In another example, for testing Trisomy 23, Down's syndrome, the concentration of human chorionic gonadotropin (hCG), estriol (E3), and alpha-fetoprotein (AFP) are measured. In a test sample, hCG is normally present in the range of mg/mL, E3 is present in the range of ng/mL, and AFP is present in the range of pg/mL. The variation in a concentration range of different analytes within a sample renders multiplex assays more challenging due to consequent variation in the dynamic range of the assay. Therefore, quantitative assay methods require balanced measurements and the need to control the reactivity of binding reagents, for analysing a sample with higher concentration of analytes and for analysing a sample containing multiple analytes at significantly different detection ranges.

Figure 11A:
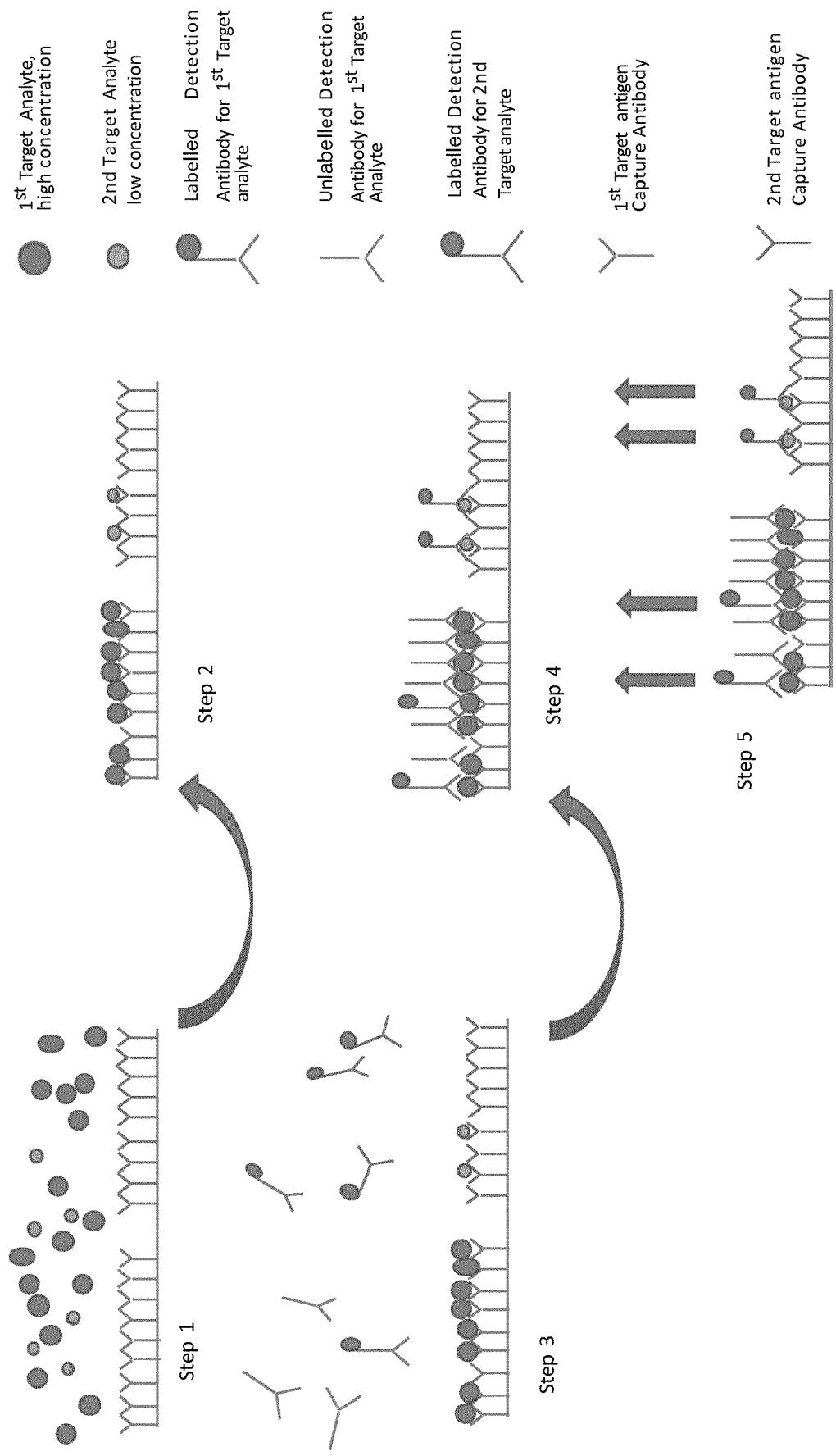
FIG. 11A is a diagrammatic representation of a method of controlling the level of detection signal in an immunoassay.
Figure 11B:
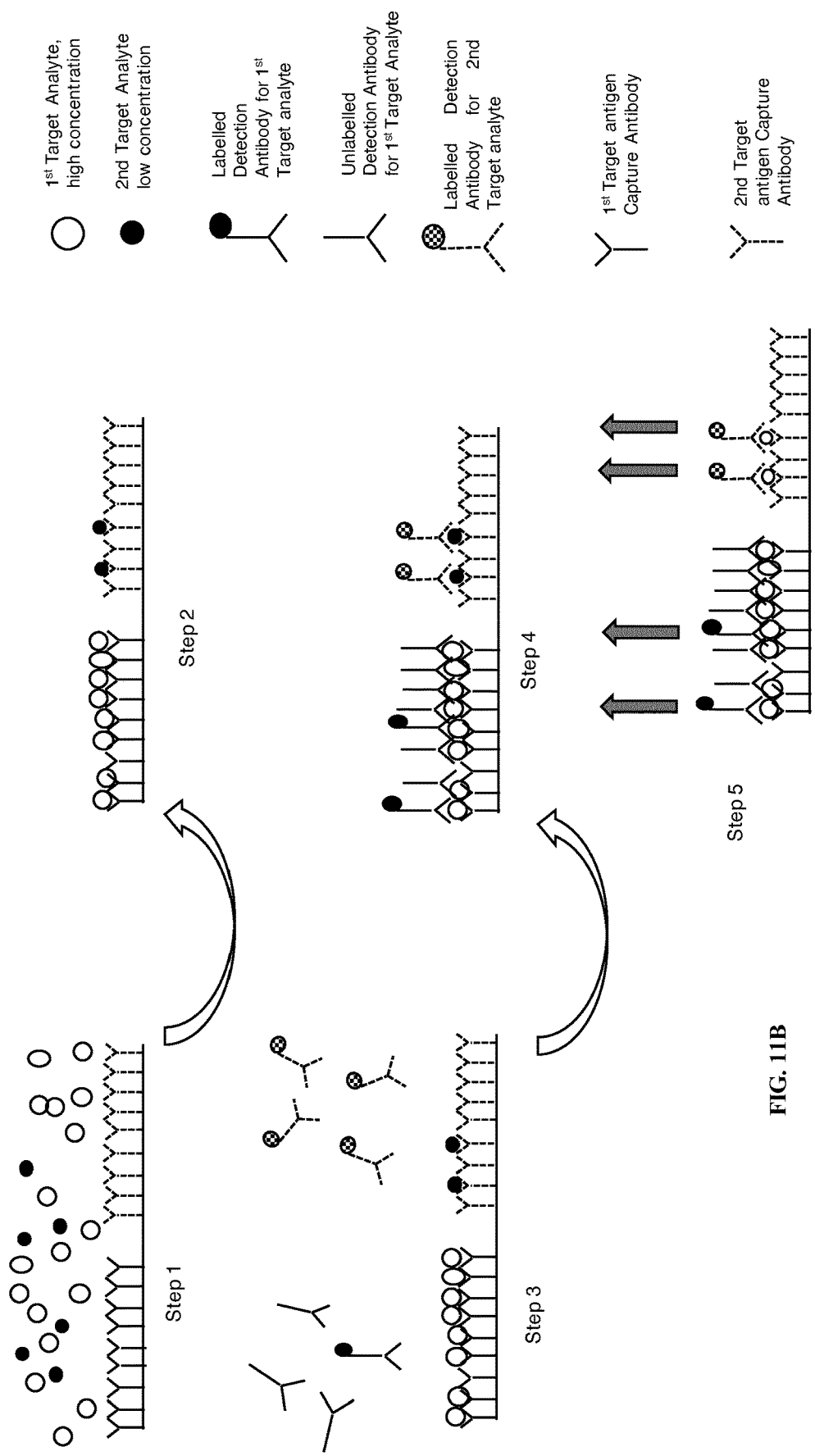
FIG. 11B is a black and white reproduction of the colour representation in FIG. 11A.

According to yet more embodiments, the technology of the present disclosure provides for a method of controlling the level of detection signal in an immunoassay. The level of a detection signal from each analyte can be precisely controlled by using known concentrations of conjugated and unconjugated binding reagents at different ratios (consider FIG. 11). The method allows for accurate quantification of multiple target analytes at wide ranges of concentrations in a sample and can be employed in singleplex assays, as well as in multiplex or multiple-singleplex assays. The method further allows balancing and/or optimizing of the ratio of conjugated binding reagent to unconjugated binding reagent according to a standard or expected concentration range of each analyte within a sample (see also FIG. 11). The sample is introduced to a solid phase with antibodies for two target analytes of different concentrations (Step 1). The first target analyte is at a high concentration whereas the second target analyte is at a low concentration. The target analytes bind to antibodies (Step 2). Detection antibodies are introduced to the solid phase wherein 25% is conjugated for analyte 1, 100% is conjugated for analyte 2 (Step 3). Detection antibodies bind to immobilised target analytes (Step 4) and subsequently the signal from analyte 1 is equalised to signal from analyte 2 to allow simultaneous analysis (Step 5).

By changing the assay signal, greater control of readout of singleplex or multiplex tests can be exercised. Accordingly, applying the present technology principles to multiplex tests, it is easier to obtain multiple results at once and have a longer development period. Ultimately, this leads to a more precise measurement of concentration. In one embodiment, this would allow the assay signals of various thyroid biomarkers, TSH, T3, and T4 to be changed to be the same (or have very similar ranges) even though concentrations are different. By knowing the conjugated vs. unconjugated levels of antibody, it is possible to determine the concentrations of each antibody individually in the mixture.

In an alternate embodiment, the present technology relates to a method for controlling the dynamic range of an assay by controlling the level of detection signal. The method comprises the steps of: i) providing a solid phase immobilized with a binding reagent, specific for a target analyte; ii) contacting the solid phase with a mixture of a sample comprising target analyte and a conjugated analyte; iii) incubating the solid phase in contact with the mixture under optimum conditions for interaction; and iv) measuring the interaction between the immobilized binding reagent and the mixture, wherein dynamic range of the assay is controlled by adjusting the ratio of the sample analyte to the conjugated analyte in the mixture. The target analytes present in the sample can be quantitatively determined by controlling the dynamic range of the assay.

For example, the target analyte to be tested may comprise a protein. Further, the mixture may include a sample containing target protein mixed with a known concentration of the same protein conjugated with an enzyme such as HRP. The mixture further reacts with a solid phase immobilized with an antibody specific to the protein, under optimal conditions for protein-antibody binding. The enzyme labelled protein competes with target protein in the sample for binding to target sites on immobilized antibody and the difference in binding the proteins in the mixture is measured by detection signals produced by the enzyme upon adding a suitable substrate.

The level of detection signals can be controlled by optimizing the ratio of conjugated analyte to target analyte in the sample. For example, the higher concentration of conjugated analyte than target analyte in a sample results in increased binding of conjugated analyte to the immobilized binding reagent, thus increasing detection signals. Similarly, a ratio of the mixture containing a higher concentration of the target analyte and a lower concentration of conjugated analyte results in increased binding of target analyte to the immobilized binding reagent, thus providing reduced detection signals. For instance, the detection signal may comprise colour changes of added substrate due to the enzymatic activity of the conjugate. The change in intensity of colour indicates the difference in binding among the target analyte and conjugated analyte to the immobilized binding reagent or detection reagent.

In yet another embodiment, the present technology provides a system for quantitative detection of one or more analytes by controlling the dynamic range of an immunoassay. The system comprises a container or a mixer for providing target analytes to biological sample and contacting the target analytes with a mixture of a conjugated binding reagent and an unconjugated binding reagent. In some embodiments, the container or mixer can allow reacting the mixture having a conjugated binding reagent and an unconjugated binding reagent at different predetermined ratios with one or more analytes immobilized on a solid phase. However, the solid phase is not required to all embodiments to all embodiments described herein, and accordingly the present disclosure is not limited to the use of the solid phase.

The system further includes a sensor configured to measure the interaction between the one or more target analytes and the mixture of the conjugated binding reagent and the unconjugated binding reagent. For example, the sensor can determine a first concentration of the conjugated binding reagent reacting with the analytes on the solid phase and a second concentration of the unconjugated binding reagent reacting with the analytes on the solid phase.

The system further includes controller configured to control a dynamic range of assay signals by adjusting a ratio of the conjugated binding reagent and the unconjugated binding reagent in the mixture. The system may further include an analyser configured to determine a concentration of each of the target analytes. For example, the analyser can quantitatively determine one or more target analytes by analysing the first concentration and second concentration of the binding reagents for each ratio of the mixture.

The sensor may comprise a colorimetric, fluorimetric, photometric, and/or spectrophotometric devices adapted for measuring or quantifying detection signals produced by the binding reagents interacting with target analytes. The controller may also comprise a computing device operatively connected to the sensor of the system. In some embodiments, the computing device includes at least one processor and a memory, which stores processor executable instructions, which when executed by the least one processor cause the system to make measurements by the sensor, change a ratio of the mixture, and quantitatively determine the one or more target analytes. In some embodiments, the analyser also includes a computing device such as a personal computer or a laptop. In yet more embodiments, the controller and analyser can be combined together in a single device. For example, one computing device can be used as the controller and the analyser.

The container may comprise a microtiter plate, microstrip, glass tube, and/or similar devices adapted to receive or mix reagents with analytes or sample containing one or more analytes.

In an embodiment, the analyser determines the concentration of a target analyte in a sample based on the difference between multiple concentration values of binding reagents interacting with the solid phase, for different predetermined ratios of conjugated and unconjugated binding reagent in the mixture. The dynamic range of the assay is controlled or modified by adjusting the ratios of the mixture containing binding reagents. Thus, the sensitivity of the assay is controlled for determining the concentration of one or more analytes in the sample.

The methods and systems of the present disclosure relating to quantitative determination of analytes by controlling the level of detection signal or controlling the dynamic range of an assay can be employed in a variety of immunoassays (e.g., bead-based assay, microtiter plate-based assay or microstrip based assay), microarrays (e.g., protein microarray, DNA microarray, RNA microarray), protein biochip assay, antibody array, and in assays performed using microfluidic devices. These assays may typically be biological assays, but not necessarily, as the principle methods of this disclosure may be applied to any molecular or other chemical detection.

According to certain embodiments, the present technology can be also configured to determine diseases of a subject, whose fluid samples were tested and analysed using the methods described herein. For example, measurement of troponin and B-type natriuretic peptide (BNP) biomarkers using the methods disclosed herein could lead to a determination of congestive heart failure and subsequent treatment with warfarin. Moreover, the present technology may provide automatic recommendations, suggestions, or plans for treating identified diseases. In particular, various diseases can be determined based on the results of quantitative detection of one or more target analytes in biological samples as described herein.

Thus, methods and systems for differentiating and/or identifying cells or other components in biological samples have been described and methods and systems for quantitative detection of one or more target analytes in a biological sample by controlling the dynamic range of assay signals have been described. Although embodiments have been described with reference to specific example embodiments, it will be evident that various modifications and changes can be made to these example embodiments without departing from the broader spirit and scope of the present application. Accordingly, the specification and drawings are to be regarded in an illustrative rather than a restrictive sense.

As used herein, by "synthetic" is meant not naturally occurring but made through human technical intervention. In the context of synthetic proteins, peptides and nucleic acids, this encompasses molecules produced by recombinant, chemical synthetic or combinatorial techniques as are well understood in the art.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

The invention claimed is:

1. A method for quantitative detection of one or more target analytes in a biological sample by controlling a dynamic range of assay signals in an enzyme-linked immunosorbent assay (ELISA), the method comprising:

providing one or more target analytes in a sample, the one or more target analytes selected from the group consisting of one or more of an antigen, an antibody, a nucleic acid, a carbohydrate, a lipid, a peptide, a protein, a polymer, and any combination thereof;

contacting the one or more target analytes with a mixture of first binding reagents that undergo binding interaction with the one or more target analytes to form conjugated analytes, and second binding reagents that do not undergo binding interaction with the one or more target analytes thereby forming unconjugated analytes, wherein the conjugated first binding reagents and the second binding reagents each having predetermined concentrations are specific to the one or more target analytes;

measuring the binding interaction between the one or more target analytes and conjugated first binding reagents and the one or more target analytes and unconjugated second binding reagents in the mixture;

adjusting a ratio of the conjugated first binding reagents and the unconjugated second binding reagents in the mixture to control a dynamic range of measurable assay signals selected from the group consisting of color change, fluorescent signals, and chemiluminescent signals, the ratio selected from the group consisting of a molar ratio, a weight ratio and a volumetric ratio, and any combinations thereof; and quantitatively determining the one or more target analytes in the sample based on both a) results of the measuring step of the binding interaction, and b) based on the controlling of the dynamic range of the assay signals, wherein adjusting the ratio of the conjugated first binding reagents and the unconjugated second binding reagents in the mixture is executed by a computing device.

2. The method of claim 1, further comprising determining a concentration of each of the target analytes.

3. The method of claim 1, further comprising adding additional conjugated analytes to the sample; thereby causing dilution of the one or more target analytes.

4. The method of claim 1, further comprising adding additional unconjugated analytes to the sample; thereby causing dilution of the one or more target analytes.

5. The method of claim 1, wherein the conjugated first binding reagents or the unconjugated second binding reagents comprise one or more of an antibody, an antigen, an aptamer, a peptide, a protein, and an oligonucleotide.

6. The method of claim 1, wherein conjugated binding reagents comprise a binding reagent coupled with a conjugate selected from a group consisting of: an enzyme, a protein, a peptide, a fluorophore, a streptavidin, an avidin, an antibody, an antigen, an aptamer, and an oligonucleotide, and any combinations thereof.

7. The method of claim 1, wherein the sample comprises a non-biological fluid.

* * * * *